United States Patent [19]

Miracle et al.

[11] Patent Number: 5,817,614
[45] Date of Patent: *Oct. 6, 1998

[54] COLOR-SAFE BLEACH BOOSTERS, COMPOSITIONS AND LAUNDRY METHODS EMPLOYING SAME

[75] Inventors: Gregory Scot Miracle, Hamilton; Robert Richard Dykstra, Fairfield, both of Ohio

[73] Assignee: Procter & Gamble Company, Cincinnati, Ohio

[*] Notice: The term of this patent shall not extend beyond the expiration date of Pat. No. 5,576,282.

[21] Appl. No.: 697,743

[22] Filed: Aug. 29, 1996

[51] Int. Cl.$^6$ ................ C11D 3/28; C11D 3/39; C07D 217/00
[52] U.S. Cl. ............ 510/376; 252/186.38; 252/186.39; 252/186.42; 252/183.43; 510/276; 510/302; 510/305; 510/309; 510/312; 510/314; 510/494; 510/504; 546/150
[58] Field of Search .................... 510/376, 276, 510/302, 305; 252/186.38, 186.39, 186.42, 186.43; 546/150

[56] References Cited

U.S. PATENT DOCUMENTS

| | | | |
|---|---|---|---|
| Re. 28,034 | 6/1974 | Gray | 260/283 S |
| 5,045,223 | 9/1991 | Batel et al. | 252/102 |
| 5,360,568 | 11/1994 | Madison et al. | 252/102 |
| 5,360,569 | 11/1994 | Madison et al. | 252/102 |
| 5,370,826 | 12/1994 | Madison et al. | 252/102 |
| 5,442,066 | 8/1995 | Madison et al. | 546/16 |
| 5,478,357 | 12/1995 | Madison et al. | 8/111 |
| 5,482,515 | 1/1996 | Madison et al. | 8/111 |
| 5,550,256 | 8/1996 | Madison et al. | 548/473 |

FOREIGN PATENT DOCUMENTS

| | | | |
|---|---|---|---|
| 0446981 | 9/1991 | European Pat. Off. | C11D 3/395 |
| 0446982 | 9/1991 | European Pat. Off. | C11D 3/39 |
| 1215656 | 12/1970 | Hungary | 546/150 |
| 978281 | 12/1964 | United Kingdom | 546/150 |
| WO 95/13352 | 5/1995 | WIPO | C11D 3/39 |
| WO 95/13353 | 5/1995 | WIPO | C11D 3/39 |

*Primary Examiner*—Mukund J. Shah
*Assistant Examiner*—Deepak R. Rao
*Attorney, Agent, or Firm*—Brian M. Bolam; K. W. Zerby; Richard S. Echler, Sr.

[57] ABSTRACT

Bleach boosters comprising quaternary imine zwitterions are disclosed. The bleach boosters increase bleaching effectiveness in lower temperature solutions and demonstrate superior color safety profiles. The bleach boosters are ideally suited for inclusion into bleaching compositions including those with detersive surfactants and enzymes. Also provided is a laundry additive product including quaternary imine zwitterions. A method for laundering a fabric employing the bleach boosters of the present invention is also disclosed.

19 Claims, No Drawings

COLOR-SAFE BLEACH BOOSTERS, COMPOSITIONS AND LAUNDRY METHODS EMPLOYING SAME

FIELD OF THE INVENTION

This invention relates to color-safe bleach boosters, compositions and laundry methods employing color-safe bleach boosters. More particularly, this invention relates to quaternary imine bleach boosters, compositions and laundry methods employing quaternary imine bleach boosters.

BACKGROUND OF THE INVENTION

Oxygen bleaching agents have become increasingly popular in recent years in household and personal care products to facilitate stain and soil removal. Bleaches are particularly desirable for their stain-removing, dingy fabric cleanup, whitening and sanitization properties. Oxygen bleaching agents have found particular acceptance in laundry products such as detergents, in automatic dishwashing products and in hard surface cleansers. Oxygen bleaching agents, however, are somewhat limited in their effectiveness. Some frequently encountered disadvantages include color damage on fabrics and damage to laundry appliances, specifically rubber hoses these appliances may contain. In addition, oxygen bleaching agents tend to be extremely temperature rate dependent. Thus, the colder the solution in which they are employed, the less effective the bleaching action. Temperatures in excess of 60° C. are typically required for effectiveness of an oxygen bleaching agent in solution.

To solve the aforementioned temperature rate dependency, a class of compounds known as "bleach activators" has been developed. Bleach activators, typically perhydrolyzable acyl compounds having a leaving group such as oxybenzenesulfonate, react with the active oxygen group, typically hydrogen peroxide or its anion, to form a more effective peroxyacid oxidant. It is the peroxyacid compound which then oxidizes the stained or soiled substrate material. However, bleach activators are also somewhat temperature dependent. Bleach activators are more effective at warm water temperatures of from about 40° C. to about 60° C. In water temperatures of less than about 40° C., the peroxyacid compound loses some of its bleaching effectiveness.

Attempts have been made to develop a bleach system which will be effective in lower temperature water conditions. U.S. Pat. No. 5,360,568 to Madison et al., U.S. Pat. No. 5,360,569 to Madison et al., and U.S. Pat. No. 5,370,826 to Madison et al., all disclose quaternary imine salts as catalysts for peroxygen compounds to transfer active oxygen and thus increase the activity of peroxygen compounds over a range of water temperatures, including lower temperatures. However, quaternary imine salts are not completely satisfactory in laundry bleaching applications. In particular, the quaternary imine salts disclosed in these references, when combined with peroxygen compounds, cause an unacceptable level of color damage on fabrics.

Accordingly, the need remains for an effective bleach boosting agent and composition containing bleach boosters which provides effective bleaching in lower water temperatures and provides improved color-safety profiles.

SUMMARY OF THE INVENTION

This need is met by the present invention wherein color-safe bleach boosters are provided. The bleach boosters of the present invention provide superior bleaching effectiveness in lower water temperatures as well as superior color safety profiles. According to a first embodiment of the present invention, a bleaching composition is provided. The composition comprises a peroxygen source and a quaternary imine zwitterion bleach booster. Preferably, the bleach booster comprises from about 0.01% to about 10% by weight of the bleaching composition and the peroxygen source comprises from about 0.01% to about 60% by weight of the bleaching composition.

The peroxygen source may comprise a preformed peracid compound selected from the group consisting of percarboxylic acid and salts, percarbonic acids and salts, perimidic acids and salts, peroxymonosulfuric acids and salts, and mixtures thereof. Alternatively, the peroxygen source may comprise hydrogen peroxide or hydrogen peroxide in combination with a bleach activator. The hydrogen peroxide source may be selected from the group consisting of perborate compounds, percarbonate compounds, perphosphate compounds and mixtures thereof. The bleach activator may be selected from the group consisting of tetraacetylethylenediamine, sodium octanoyloxybenzene sulfonate, sodium nonanoyloxybenzene sulfonate, sodium decanoyloxybenzene sulfonate, sodium lauroyloxybenzene sulfonate, (6-octanamido-caproyl)oxybenzenesulfonate, (6-nonanamido-caproyl)oxybenzenesulfonate, (6-decanamido-caproyl)oxybenzenesulfonate, and mixtures thereof.

In general, the booster has the formula:

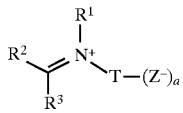

wherein $R^1$–$R^3$ is hydrogen or an unsubstituted or substituted radical selected from the group consisting of phenyl, aryl, heterocyclic ring, alkyl and cycloalkyl radicals; $R_1$ and $R_2$ form part of a common ring; T is,

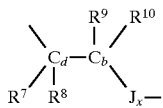

wherein x is equal to 0 or 1; J, when present, is selected from the group consisting of $-CR^{11}R^{12}-$, $-CR^{11}R^{12}CR^{13}R^{14}-$, and $-CR^{11}R^{12}CR^{13}R^{14}CR^{15}R^{16}-$; $R^7$–$R^{16}$ are individually selected from the group consisting of H, linear or branched $C_1$–$C_{18}$ substituted or unsubstituted alkyl, alkylene, oxyalkylene, aryl, substituted aryl, substituted arylcarbonyl groups, and amide groups; provided that at least one of $R^7$–$R^8$ must be H or methyl, and that when neither $R^9$ nor $R^{10}$ is H, one of $R^7$–$R^8$ must be H. Preferably, at least one of $R^9$ and $R^{10}$ must also be H; Z is covalently bonded to $J_x$ when x is 1 and to $C_b$ when x is 0, and Z is selected from the group consisting of $-CO_2^-$, $-SO_3^-$ and $-OSO_3^-$ and a is 1. $R_1$ and $R_2$ together may form the non-charged moiety:

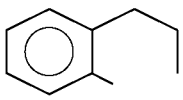

More preferably, the bleach booster is an aryliminium zwitterion and $R_3$ is H, Z is $-OSO_3^-$, a is 1. The aryliminium zwitterion may have the formula:

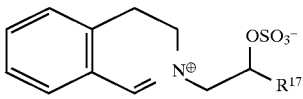

where $R^{17}$ is selected from the group consisting of H and linear or branched $C_1$–$C_{18}$ substituted or unsubstituted alkyl, preferably $C_1$–$C_{14}$ alkyl and even more preferably $C_8$–$C_{10}$ linear alkyl chain.

The bleaching composition may further include at least one detersive surfactant, at least one chelating agent, at least one detersive enzyme and preferably has a pH of about 8 to about 10.5 in a 1% solution of the bleaching composition.

In an additional embodiment of the present invention, a zwitterionic laundry bleach booster is provided. The zwitterionic laundry bleach booster is selected from:

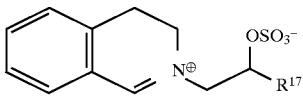

where $R^{17}$ is selected from the group consisting of H and linear or branched $C_1$–$C_{18}$ substituted or unsubstituted alkyl, preferably $C_1$–$C_{14}$ alkyl and even more preferably $C_8$–$C_{10}$ linear alkyl chain.

In accordance with yet another aspect of the present invention, a method for laundering a fabric is provided. The method comprises contacting a fabric to be laundered with a laundry solution. The laundry solution includes a peroxygen source and a bleach booster. The bleach booster is a quaternary imine zwitterion, as described above, preferably an aryliminium zwitterion.

The laundry solution may further include at least one detersive surfactant, at least one chelating agent, and at least one detersive enzyme. The pH of the laundry solution is preferably from about 8 to about 10.5. The peroxygen source may comprise either a hydrogen peroxide source or a hydrogen peroxide source in conjunction with a bleach activator. The hydrogen peroxide source may be selected from the group consisting of perborate compounds, percarbonate compounds, perphosphate compounds and mixtures thereof. The bleach activator may be selected from the group consisting of tetraacetylethylenediamine, sodium octanoyloxybenzene sulfonate, sodium nonanoyloxybenzene sulfonate, sodium decanoyloxybenzene sulfonate, sodium lauroyloxybenzene sulfonate, (6-octanamido-caproyl)oxybenzenesulfonate, (6-nonanamido-caproyl)oxybenzenesulfonate, (6-decanamido-caproyl)oxybenzenesulfonate, and mixtures thereof.

In yet another embodiment of the present invention, a laundry additive product is provided. The laundry additive product comprises a laundry additive. The laundry additive includes the bleach booster as described above. The additive is in dosage form for addition to a laundry solution.

The additive may further include a hydrogen peroxide source selected from the group consisting of perborate compounds, percarbonate compounds, perphosphate compounds and mixtures thereof. In addition, the additive may include a bleach activator selected from the group consisting of tetraacetylethylenediamine, sodium octanoyloxybenzene sulfonate, sodium nonanoyloxybenzene sulfonate, sodium decanoyloxybenzene sulfonate, sodium lauroyloxybenzene sulfonate, (6-octanamido-caproyl)oxybenzenesulfonate, (6-nonanamido-caproyl)oxybenzenesulfonate, (6-decanamido-caproyl)oxybenzenesulfonate, and mixtures thereof. The dosage form may comprise a pill, tablet, caplet, gelcap or other single dosage form. A suitable carrier may also be included in the additive.

Accordingly, it is an object of the present invention to provide a bleaching composition which demonstrates improved performance in lower temperature solutions and superior color safety on fabrics. It is a feature of the present invention to provide a bleaching composition including a bleach booster of a quaternary imine zwitterion. It is another object of the present invention to provide a method for laundering a fabric by employing a bleach booster of a quaternary imine zwitterion. It is still a further feature of the present invention to provide a laundry additive product having a bleach booster of a quaternary imine zwitterion. These, and other objects, features and advantages of the present invention will be recognized by one of ordinary skill in the art from the following description and the appended claims.

All percentages, ratios and proportions herein are on a weight basis unless otherwise indicated. All documents cited herein are hereby incorporated by reference.

DETAILED DESCRIPTION OF THE INVENTION

The present invention discloses novel and highly useful color-safe bleach boosting compounds and compositions and methods employing the novel bleach boosting compounds. The bleach boosters of the present invention provide increased bleaching effectiveness in lower temperature applications while giving superior color-safety profiles on fabrics. The bleach boosters of the present invention act in conjunction with conventional peroxygen bleaching sources to provide the above-mentioned increased bleaching effectiveness and superior color-safety profiles.

The bleach boosters of the present invention comprise quaternary imine zwitterions represented by the formula:

wherein:

$R^1$–$R^3$ may be a hydrogen or an unsubstituted or substituted radical selected from the group consisting of phenyl, aryl, heterocyclic ring, alkyl and cycloalkyl radicals;

T is

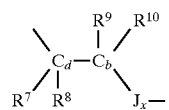

wherein x is equal to 0 or 1; J, when present, is selected from the group consisting of $-CR^{11}R^{12}-$, $-CR^{11}R^{12}CR^{13}R^{14}-$, and $-CR^{11}R^{12}CR^{13}R^{14}CR^{15}R^{16}-$; $R^7$–$R^{16}$ are individually selected from the group consisting of H, linear or branched $C_1$–$C_{18}$ substituted or unsubstituted alkyl, alkylene, oxyalkylene, aryl, substituted aryl, substituted arylcarbonyl groups, and amide groups; provided that at least one of $R^7$–$R^8$ must be H or methyl, and that when neither $R^9$ nor $R^{10}$ is H, one of $R^7$–$R^8$ must be H. Preferably, at least one of $R^9$ and $R^{10}$ must also be H. $C_b$ and $C_d$ are carbon atoms.

Z is covalently bonded to $J_x$ when x is 1 and to $C_b$ when x is 0 and is selected from the group consisting of —$CO_2^-$, —$SO_2^-$, —$PO_3^-$, —$OPO_3^-$, —$SO_3^-$ and —$OSO_3^-$ with —$OSO_3^-$ being preferred and a being 1. Accordingly, as Z is covalently bonded (when the total charge on $R^1$–$R^3$ is zero), the quaternary imine is a zwitterion.

In a more preferred embodiment, the bleach booster of the present invention is an aryliminium zwitterion. In this preferred embodiment, $R^1$ and $R^2$ together form part of a common ring. In particular, $R^1$ and $R^2$ together may form one or more five-membered, six-membered or seven-membered rings. The most preferred aryliminums are created from the non-charged moiety:

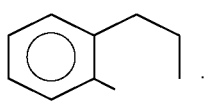
(III)

Accordingly, the preferred aryliminium zwitterions involve $R^1$ and $R^2$ together forming the non-charged moiety (III) with T being

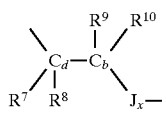

with a being 1 and Z being selected from —$OSO_3^-$ and —$SO_3^-$. More preferably, the aryliminium zwitterion of the present invention has $R^1$ and $R^2$ together forming the non-charged moiety (III) with T being:

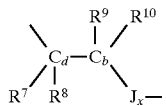

with a being 1, Z being —$OSO_3^-$. The most preferred aryliminium zwitterions according to the present invention are represented by the formula:

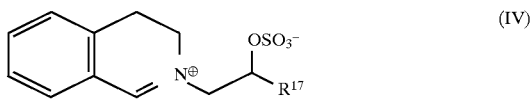
(IV)

where $R^{17}$ is selected from the group consisting of H and linear or branched $C_1$–$C_{18}$ substituted or unsubstituted alkyl, preferably $C_1$–$C_{14}$ alkyl and even more preferably $C_8$–$C_{10}$ linear alkyl chain.

The quaternary imine bleach boosters of the present invention act in conjunction with a peroxygen source to provide a more effective bleaching system. Peroxygen sources are well-known in the art and the peroxygen source employed in the present invention may comprise any of these well known sources, including peroxygen compounds as well as compounds which under consumer use conditions provide an effective amount of peroxygen in situ. The peroxygen source may include a hydrogen peroxide source, the in situ formation of a peracid anion through the reaction of a hydrogen peroxide source and a bleach activator, preformed peracid compounds or mixtures of suitable peroxygen sources. Of course, one of ordinary skill in the art will recognize that other sources of peroxygen may be employed without departing from the scope of the invention.

The preformed peracid compound as used herein is any convenient compound which is stable and which under consumer use conditions provides an effective amount of peracid anion. The bleach boosters of the present invention may of course be used in conjunction with a preformed peracid compound selected from the group consisting of percarboxylic acids and salts, percarbonic acids and salts, perimidic acids and salts, peroxymonosulfuric acids and salts, and mixtures thereof. One class of suitable organic peroxycarboxylic acids have the general formula:

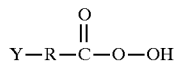

wherein R is an alkylene or substituted alkylene group containing from 1 to about 22 carbon atoms or a phenylene or substituted phenylene group, and Y is hydrogen, halogen, alkyl, aryl, —C(O)OH or —C(O)OOH.

Organic peroxyacids suitable for use in the present invention can contain either one or two peroxy groups and can be either aliphatic or aromatic. When the organic peroxycarboxylic acid is aliphatic, the unsubstituted acid has the general formula:

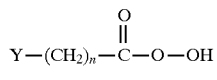

where Y can be, for example, H, $CH_3$, $CH_2Cl$, C(O)OH, or C(O)OOH; and n is an integer from 1 to 20. When the organic peroxycarboxylic acid is aromatic, the unsubstituted acid has the general formula:

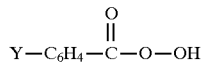

wherein Y can be, for example, hydrogen, alkyl, alkylhalogen, halogen, C(O)OH or C(O)OOH.

Typical monoperoxy acids useful herein include alkyl and aryl peroxyacids such as:
(i) peroxybenzoic acid and ring-substituted peroxybenzoic acid, e.g. peroxy-a-naphthoic acid, monoperoxyphthalic acid (magnesium salt hexahydrate), and o-carboxybenzamidoperoxyhexanoic acid (sodium salt);
(ii) aliphatic, substituted aliphatic and arylalkyl monoperoxy acids, e.g. peroxylauric acid, peroxystearic acid, N-nonanoylaminoperoxycaproic acid (NAPCA), N,N-(3-octylsuccinoyl)aminoperoxycaproic acid (SAPA) and N,N-phthaloylaminoperoxycaproic acid (PAP);
(iii) amidoperoxyacids, e.g. monononylamide of either peroxysuccinic acid (NAPSA) or of peroxyadipic acid (NAPAA).

Typical diperoxyacids useful herein include alkyl diperoxyacids and aryldiperoxyacids, such as:
(iv) 1,12-diperoxydodecanedioic acid;
(v) 1,9-diperoxyazelaic acid;
(vi) diperoxybrassylic acid; diperoxysebacic acid and diperoxyisophthalic acid;
(vii) 2-decyldiperoxybutane-1,4-dioic acid;
(viii) 4,4'-sulfonylbisperoxybenzoic acid.

Such bleaching agents are disclosed in U.S. Pat. No. 4,483,781, Hartman, issued Nov. 20, 1984, U.S. Pat. No. 4,634,551 to Burns et al., European Patent Application 0,133,354, Banks et al. published Feb. 20, 1985, and U.S. Pat. No. 4,412,934, Chung et al. issued Nov. 1, 1983. Sources also include 6-nonylamino-6-oxoperoxycaproic acid as described in U.S. Pat. No. 4,634,551, issued Jan. 6, 1987 to Burns et al. Persulfate compounds such as for example OXONE, manufactured commercially by E. I. DuPont de Nemours of Wilmington, Del. can also be employed as a suitable source of peroxymonosulfuric acid.

A source of hydrogen peroxide as used herein is any convenient compound or mixture which under consumer use conditions provides an effective amount of hydrogen peroxide. Levels in general may vary widely and are typically from about 0.5% to about 70%, more typically from about 0.5% to about 25%, by weight of the bleaching compositions herein. The source of hydrogen peroxide used herein can be any convenient source, including hydrogen peroxide itself. For example, perborate, e.g., sodium perborate (any hydrate but preferably the mono- or tetra-hydrate), sodium carbonate peroxyhydrate or equivalent percarbonate salts, sodium pyrophosphate peroxyhydrate, urea peroxyhydrate, or sodium peroxide can be used herein. Mixtures of convenient hydrogen peroxide sources can also be used.

A preferred percarbonate bleach comprises dry particles having an average particle size in the range from about 500 micrometers to about 1,000 micrometers, not more than about 10% by weight of said particles being smaller than about 200 micrometers and not more than about 10% by weight of said particles being larger than about 1,250 micrometers. Optionally, the percarbonate can be coated with silicate, borate or water-soluble surfactants. Percarbonate is available from various commercial sources such as FMC, Solvay and Tokai Denka.

A bleach activator as used herein is any compound which when used in conjunction with a hydrogen peroxide source leads to the in situ production of the peracid corresponding to the bleach activator. Various non limiting examples of activators are disclosed in U.S. Pat. No. 4,915,854, issued Apr. 10, 1990 to Mao et al. and U.S. Pat. No. 4,412,934. The nonanoyloxybenzene sulfonate (NOBS) and tetraacetylethylenediamine (TAED) activators are typical, and mixtures thereof can also be used. See also U.S. Pat. No. 4,634,551 for other typical bleaches and activators useful herein.

Highly preferred amido-derived bleach activators are those of the formulae:

$$R^1N(R^5)C(O)R^2C(O)L \text{ or } R^1C(O)N(R^5)R^2C(O)L$$

wherein as used for these compounds $R^1$ is an alkyl group containing from about 6 to about 12 carbon atoms, $R^2$ is an alkylene containing from 1 to about 6 carbon atoms, $R^5$ is H or alkyl, aryl, or alkaryl containing from about 1 to about 10 carbon atoms, and L is any suitable leaving group. A leaving group is any group that is displaced from the bleach activator as a consequence of the nucleophilic attack on the bleach activator by the hydroperoxide anion. A preferred leaving group is oxybenzenesulfonate.

Preferred examples of bleach activators of the above formulae include (6-octanamidocaproyl) oxybenzenesulfonate, (6-nonanamidocaproyl) oxybenzenesul-fonate, (6-decanamidocaproyl) oxybenzenesulfonate, and mixtures thereof as described in U.S. Pat. No. 4,634,551, incorporated herein by reference.

Another class of bleach activators comprises the benzoxazin-type activators disclosed by Hodge et al. in U.S. Pat. No. 4,966,723, issued Oct. 30, 1990, incorporated herein by reference. A highly preferred activator of the benzoxazin-type is:

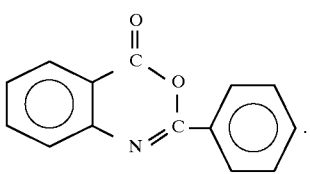

Still another class of preferred bleach activators includes the acyl lactam activators, especially acyl caprolactams and acyl valerolactams of the formulae:

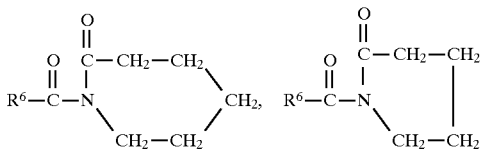

wherein as used for these compounds $R^6$ is H or an alkyl, aryl, alkoxyaryl, or alkaryl group containing from 1 to about 12 carbon atoms. Highly preferred lactam activators include benzoyl caprolactam, octanoyl caprolactam, 3,5,5-trimethylhexanoyl caprolactam, nonanoyl caprolactam, decanoyl caprolactam, undecenoyl caprolactam, benzoyl valerolactam, octanoyl valerolactam, decanoyl valerolactam, undecenoyl valerolactam, nonanoyl valerolactam, 3,5,5-trimethylhexanoyl valerolactam and mixtures thereof. See also U.S. Pat. No. 4,545,784, issued to Sanderson, Oct. 8, 1985, incorporated herein by reference, which discloses acyl caprolactams, including benzoyl caprolactam, adsorbed into sodium perborate.

The quaternary imine bleach booster of the present invention acts in conjunction with a peroxygen source to increase bleaching effectiveness. Without being bound by theory, it is believed that the bleach booster reacts with the peroxygen source to form a more active bleaching species, a quaternary oxaziridinium compound. The formed oxaziridinium compounds are also zwitterionic. The oxaziridinium compound has an increased activity at lower temperatures relative to the peroxygen compound. The oxaziridinium compound is represented by the formula:

(VIII)

wherein $R^4$ is $-T-(Z^-)_a$ where T, Z and a are defined as above and can be produced from the quaternary imine of the present invention with the reaction:

(I)                                                     (VIII)

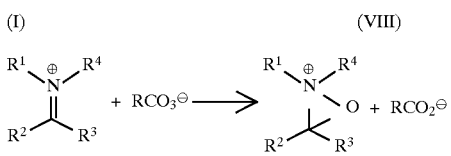

Thus, the preferred bleach booster of the present invention represented by the formula (IV) produces the active oxaziridinium bleaching species represented by the formula:

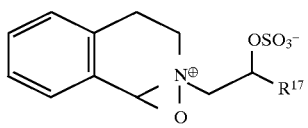

wherein $R^{17}$ is defined as above.

The bleach boosters of the present invention may be employed in conjunction with a peroxygen source in a bleaching composition. In a composition, the peroxygen source may be present in levels of from about 0.1% to about 60% by weight of the composition, and preferably from about 1% to about 40% by weight of the composition. In a composition, the bleach booster may be present from about 0.01% to about 10% by weight of the composition, and more preferably from about 0.05% to about 5% by weight of the composition.

The bleaching composition of the present invention may be advantageously employed in laundry applications, hard surface cleaning, automatic dishwashing applications, as well as cosmetic applications such as dentures, teeth, hair and skin. However, due to the unique advantages of both increased effectiveness in lower temperature solutions and the superior color-safety profile, the bleach boosters of the present invention are ideally suited for laundry applications such as the bleaching of fabrics through the use of bleach containing detergents or laundry bleach additives. Furthermore, the bleach boosters of the present invention may be employed in both granular and liquid compositions.

Accordingly, the bleaching compositions of the present invention may include various additional ingredients which are desirable in laundry applications. Such ingredients include detersive surfactants, bleach catalysts, builders, chelating agents, enzymes, polymeric soil release agents, brighteners and various other ingredients. Compositions including any of these various additional ingredients preferably have a pH of from about 8 to about 10.5 in a 1% solution of the bleaching composition.

Detersive Surfactant—The bleaching compositions of the present invention may include a detersive surfactant. Detersive surfactants included in the fully-formulated compositions afforded by the present invention comprise at least 1%, preferably from about 1% to about 99.8%, by weight of the composition depending upon the particular surfactants used and the effects desired. In a highly preferred embodiment, the detersive surfactant comprises from about 5% to about 80% by weight of the composition.

The detersive surfactant can be nonionic, anionic, ampholytic, zwitterionic, or cationic. Mixtures of these surfactants can also be used. Preferred detergent compositions comprise anionic detersive surfactants or mixtures of anionic surfactants with other surfactants, especially nonionic surfactants.

Nonlimiting examples of surfactants useful herein include the conventional $C_{11}$–$C_{18}$ alkyl benzene sulfonates and primary, secondary and random alkyl sulfates, the $C_{10}$–$C_{18}$ alkyl alkoxy sulfates, the $C_{10}$–$C_{18}$ alkyl polyglycosides and their corresponding sulfated polyglycosides, $C_{12}$–$C_{18}$ alpha-sulfonated fatty acid esters, $C_{12}$–$C_{18}$ alkyl and alkyl phenol alkoxylates (especially ethoxylates and mixed One class of nonionic surfactant particularly useful in bleaching compositions of the present invention is condensates of ethylene oxide with a hydrophobic moiety to provide a surfactant having an average hydrophilic-lipophilic balance (HLB) in the range of from 5 to 17, preferably from 6 to 14, more preferably from 7 to 12. The hydrophobic (lipophilic) moiety may be aliphatic or aromatic in nature. The length of the polyoxyethylene group which is condensed with any particular hydrophobic group can be readily adjusted to yield a water-soluble compound having the desired degree of balance between hydrophilic and hydrophobic elements.

Especially preferred nonionic surfactants of this type are the $C_9$–$C_{15}$ primary alcohol ethoxylates containing 3–8 moles of ethylene oxide per mole of alcohol, particularly the $C_{14}$–$C_{15}$ primary alcohols containing 6–8 moles of ethylene oxide per mole of alcohol, the $C_{12}$–$C_{15}$ primary alcohols containing 3–5 moles of ethylene oxide per mole of alcohol, and mixtures thereof.

Another suitable class of nonionic surfactants comprises the polyhydroxy fatty acid amides of the formula:

wherein: $R^1$ is H, $C_1$–$C_8$ hydrocarbyl, 2-hydroxyethyl, 2-hydroxypropyl, or a mixture thereof, preferably $C_1$–$C_4$ alkyl, more preferably $C_1$ or $C_2$ alkyl, most preferably $C_1$ alkyl (i.e., methyl); and $R^2$ is a $C_5$–$C_{32}$ hydrocarbyl moiety, preferably straight chain $C_7$–$C_{19}$ alkyl or alkenyl, more preferably straight chain $C_9$–$C_{17}$ alkyl or alkenyl, most preferably straight chain $C_{11}$–$C_{19}$ alkyl or alkenyl, or mixture thereof; and Z is a polyhydroxyhydrocarbyl moiety having a linear hydrocarbyl chain with at least 2 (in the case of glyceraldehyde) or at least 3 hydroxyls (in the case of other reducing sugars) directly connected to the chain, or an alkoxylated derivative (preferably ethoxylated or propoxylated) thereof. Z preferably will be derived from a reducing sugar in a reductive amination reaction; more preferably Z is a glycityl moiety. Suitable reducing sugars include glucose, fructose, maltose, lactose, galactose, mannose, and xylose, as well as glyceraldehyde. As raw materials, high dextrose corn syrup, high fructose corn syrup, and high maltose corn syrup can be utilized as well as the individual sugars listed above. These corn syrups may yield a mix of sugar components for Z. It should be understood that it is by no means intended to exclude other suitable raw materials. Z preferably will be selected from the group consisting of —$CH_2$—$(CHOH)_n$—$CH_2OH$, —CH($CH_2OH$)—$(CHOH)_{n-1}$—$CH_2OH$, —$CH_2$—$(CHOH)_2$(CHOR')(CHOH)—$CH_2OH$, where n is an integer from 1 to 5, inclusive, and R' is H or a cyclic mono- or polysaccharide, and alkoxylated derivatives thereof. Most preferred are glycityls wherein n is 4, particularly —$CH_2$—$(CHOH)_4$—$CH_2OH$.

In Formula (I), $R^1$ can be, for example, N-methyl, N-ethyl, N-propyl, N-isopropyl, N-butyl, N-isobutyl, N-2-hydroxy ethyl, or N-2-hydroxy propyl. For highest sudsing, $R^1$ is preferably methyl or hydroxyalkyl. If lower sudsing is desired, $R^1$ is preferably $C_2$–$C_8$ alkyl, especially n-propyl, iso-propyl, n-butyl, iso-butyl, pentyl, hexyl and 2-ethyl hexyl.

$R^2$—CO—N< can be, for example, cocamide, stearamide, oleamide, lauramide, myristamide, capricamide, palmitamide, tallowamide, etc.

Conventional Detersive Adjuncts—While not essential for the purposes of the present invention, several conventional adjuncts illustrated hereinafter are suitable for use in the instant compositions and may be desirably incorporated in preferred embodiments of the invention, for example to assist or enhance cleaning performance, for treatment of the substrate to be cleaned, or to modify the aesthetics of the bleaching composition as is the case with perfumes, colorants, dyes or the like. The precise nature of these additional components, and levels of incorporation thereof, will depend on the physical form of the composition and the nature of the cleaning operation for which it is to be used. Unless otherwise indicated, the bleaching compositions of the invention may for example, be formulated as granular or power-form all-purpose or "heavy-duty" washing agents, especially laundry detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tabletted, granular, liquid and rinse-aid types for household and institutional use; liquid cleaning and disinfecting agents, including antibacterial hand-wash types, laundry bars, mouthwashes, denture cleaners, car or carpet shampoos, bathroom cleaners; hair shampoos and hair-rinses; shower gels and foam baths and metal cleaners; as well as cleaning auxilliaries such as bleach additives and "stain-stick" or pre-treat types.

Bleach catalysts—If desired, the bleach composition of the present invention can be catalyzed by means of a manganese compound. Such compounds are well known in the art and include, for example, the manganese-based catalysts disclosed in U.S. Pat. No. 5,246,621, U.S. Pat. No. 5,244,594; U.S. Pat. No. 5,194,416; U.S. Pat. No. 5,114,606; and European Pat. No. App. Pub. Nos. 549,271A1, 549,272A1, 544,440A2, and 544,490A1; Preferred examples of these catalysts include $Mn^{IV}_2(u\text{-}O)_3(1,4,7\text{-trimethyl-}1,4,7\text{-triazacyclononane})_2\text{-}(PF_6)_2$, $Mn^{III}_2(u\text{-}O)_1(u\text{-}OAc)_2(1,4,7\text{-trimethyl-}1,4,7\text{-triazacyclononane})_2(ClO_4)_2$, $Mn^{IV}_4(u\text{-}O)_6(1,4,7\text{-triazacyclononane})_4(ClO_4)_4$, $Mn^{III}\text{-}Mn^{IV}_4\text{-}(u\text{-}O)_1(u\text{-}OAc)_2\text{-}(1,4,7\text{-trimethyl-}1,4,7\text{-triazacyclo-nonane})_2\text{-}(ClO_4)_3$, $Mn^{IV}\text{-}(1,4,7\text{-trimethyl-}1,4,7\text{-triazacyclo-nonane})\text{-}(OCH_3)_3$ $(PF_6)$, and mixtures thereof. Other metal-based bleach catalysts include those disclosed in U.S. Pat. No. 4,430,243 and U.S. Pat. No. 5,114,611. The use of manganese with various complex ligands to enhance bleaching is also reported in the following U.S. Pat. Nos. 4,728,455; 5,284,944; 5,246,612; 5,256,779; 5,280,117; 5,274,147; 5,153,161; and 5,227,084.

Said manganese can be precomplexed with ethylenediaminedisuccinate or separately added, for example as a sulfate salt, with ethylenediaminedisuccinate. Other preferred transition metals in said transition-metal-containing bleach catalysts include iron or copper.

As a practical matter, and not by way of limitation, the bleaching compositions and processes herein can be adjusted to provide on the order of at least one part per ten million of the active bleach catalyst species in the aqueous washing liquor, and will preferably provide from about 0.1 ppm to about 700 ppm, more preferably from about 1 ppm to about 50 ppm, of the catalyst species in the laundry liquor.

Builders—Detergent builders can optionally be included in the compositions herein to assist in controlling mineral hardness. Inorganic as well as organic builders can be used. Builders are typically used in fabric laundering compositions to assist in the removal of particulate soils.

The level of builder can vary widely depending upon the end use of the composition and its desired physical form. When present, the compositions will typically comprise at least about 1% builder. Liquid formulations typically comprise from about 5% to about 50%, more typically about 5% to about 30%, by weight, of detergent builder. Granular formulations typically comprise from about 10% to about 80%, more typically from about 15% to about 50% by weight, of the detergent builder. Lower or higher levels of builder, however, are not meant to be excluded.

Inorganic or P-containing detergent builders include, but are not limited to, the alkali metal, ammonium and alkanolammonium salts of polyphosphates (exemplified by the tripolyphosphates, pyrophosphates, and glassy polymeric metaphosphates), phosphonates, phytic acid, silicates, carbonates (including bicarbonates and sesquicarbonates), sulphates, and aluminosilicates. However, non-phosphate builders are required in some locales. Importantly, the compositions herein function surprisingly well even in the presence of the so-called "weak" builders (as compared with phosphates) such as citrate, or in the so-called "underbuilt" situation that may occur with zeolite or layered silicate builders.

Examples of silicate builders are the alkali metal silicates, particularly those having a $SiO_2:Na_2O$ ratio in the range 1.6:1 to 3.2:1 and layered silicates, such as the layered sodium silicates described in U.S. Pat. No. 4,664,839, issued May 12, 1987 to H. P. Rieck. NaSKS-6 is the trademark for a crystalline layered silicate marketed by Hoechst (commonly abbreviated herein as "SKS-6"). Unlike zeolite builders, the Na SKS-6 silicate builder does not contain aluminum. NaSKS-6 has the delta-$Na_2SiO_5$ morphology form of layered silicate. It can be prepared by methods such as those described in German DE-A-3,417,649 and DE-A-3,742,043. SKS-6 is a highly preferred layered silicate for use herein, but other such layered silicates, such as those having the general formula $NaMSi_xO_{2x+1}.yH_2O$ wherein M is sodium or hydrogen, x is a number from 1.9 to 4, preferably 2, and y is a number from 0 to 20, preferably 0 can be used herein. Various other layered silicates from Hoechst include NaSKS-5, NaSKS-7 and NaSKS-11, as the alpha, beta and gamma forms. As noted above, the delta-$Na_2SiO_5$ (NaSKS-6 form) is most preferred for use herein. Other silicates may also be useful such as for example magnesium silicate, which can serve as a crispening agent in granular formulations, as a stabilizing agent for oxygen bleaches, and as a component of suds control systems.

Examples of carbonate builders are the alkaline earth and alkali metal carbonates as disclosed in German Patent Application No. 2,321,001 published on Nov. 15, 1973.

Aluminosilicate builders are useful in the present invention. Aluminosilicate builders are of great importance in most currently marketed heavy duty granular detergent compositions, and can also be a significant builder ingredient in liquid detergent formulations. Aluminosilicate builders include those having the empirical formula:

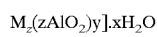

$M_z(zAlO_2)y].xH_2O$ wherein z and y are integers of at least 6, the molar ratio of z to y is in the range from 1.0 to about 0.5, and x is an integer from about 15 to about 264.

Useful aluminosilicate ion exchange materials are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669, Krummel, et al, issued Oct. 12, 1976. Preferred synthetic crystalline aluminosilicate ion exchange materials useful herein are available under the designations Zeolite A, Zeolite P (B), Zeolite MAP and Zeolite X. In an especially preferred embodiment, the crystalline aluminosilicate ion exchange material has the formula:

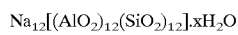

$Na_{12}[(AlO_2)_{12}(SiO_2)_{12}].xH_2O$ wherein x is from about 20 to about 30, especially about 27. This material is known as Zeolite A. Dehydrated zeolites (x=0–10) may also be used herein. Preferably, the aluminosilicate has a particle size of about 0.1–10 microns in diameter.

Organic detergent builders suitable for the purposes of the present invention include, but are not restricted to, a wide variety of polycarboxylate compounds. As used herein, "polycarboxylate" refers to compounds having a plurality of carboxylate groups, preferably at least 3 carboxylates. Polycarboxylate builder can generally be added to the composition in acid form, but can also be added in the form of a neutralized salt. When utilized in salt form, alkali metals, such as sodium, potassium, and lithium, or alkanolammonium salts are preferred.

Included among the polycarboxylate builders are a variety of categories of useful materials. One important category of polycarboxylate builders encompasses the ether polycarboxylates, including oxydisuccinate, as disclosed in Berg, U.S. Pat. No. 3,128,287, issued Apr. 7, 1964, and Lamberti et al, U.S. Pat. No. 3,635,830, issued Jan. 18, 1972. See also "TMS/TDS" builders of U.S. Pat. No. 4,663,071, issued to Bush et al, on May 5, 1987. Suitable ether polycarboxylates also include cyclic compounds, particularly alicyclic compounds, such as those described in U.S. Pat. Nos. 3,923,679; 3,835,163; 4,158,635; 4,120,874 and 4,102,903.

Other useful detergency builders include the ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Citrate builders, e.g., citric acid and soluble salts thereof (particularly sodium salt), are polycarboxylate builders of particular importance for heavy duty liquid detergent formulations due to their availability from renewable resources and their biodegradability. Citrates can also be used in granular compositions, especially in combination with zeolite and/or layered silicate builders. Oxydisuccinates are also especially useful in such compositions and combinations.

Also suitable in the detergent compositions of the present invention are the 3,3-dicarboxy-4-oxa-1,6-hexanedioates and the related compounds disclosed in U.S. Pat. No. 4,566,984, Bush, issued Jan. 28, 1986. Useful succinic acid builders include the $C_5$–$C_{20}$ alkyl and alkenyl succinic acids and salts thereof. A particularly preferred compound of this type is dodecenylsuccinic acid. Specific examples of succinate builders include: laurylsuccinate, myristylsuccinate, palmitylsuccinate, 2-dodecenylsuccinate (preferred), 2-pentadecenylsuccinate, and the like. Laurylsuccinates are the preferred builders of this group, and are described in European Patent Application 86200690.5/0,200,263, published Nov. 5, 1986.

Other suitable polycarboxylates are disclosed in U.S. Pat. No. 4,144,226, Crutchfield et al, issued Mar. 13, 1979 and in U.S. Pat. No. 3,308,067, Diehl, issued Mar. 7, 1967. See also Diehl U.S. Pat. No. 3,723,322.

Fatty acids, e.g., $C_{12}$–$C_{18}$ monocarboxylic acids, can also be incorporated into the compositions alone, or in combination with the aforesaid builders, especially citrate and/or the succinate builders, to provide additional builder activity. Such use of fatty acids will generally result in a diminution of sudsing, which should be taken into account by the formulator.

In situations where phosphorus-based builders can be used, and especially in the formulation of bars used for hand-laundering operations, the various alkali metal phosphates such as the well-known sodium tripolyphosphates, sodium pyrophosphate and sodium orthophosphate can be used. Phosphonate builders such as ethane-1-hydroxy-1,1-diphosphonate and other known phosphonates (see, for example, U.S. Pat. Nos. 3,159,581; 3,213,030; 3,422,021; 3,400,148 and 3,422,137) can also be used.

Enzymes—Enzymes can be included in the formulations herein for a wide variety of fabric laundering purposes, including removal of protein-based, carbohydrate-based, or triglyceride-based stains, for example, and for the prevention of refugee dye transfer, and for fabric restoration. The enzymes to be incorporated include proteases, amylases, lipases, cellulases, and peroxidases, as well as mixtures thereof. Other types of enzymes may also be included. They may be of any suitable origin, such as vegetable, animal, bacterial, fungal and yeast origin. However, their choice is governed by several factors such as pH-activity and/or stability optima, thermostability, stability versus active detergents, builders and so on. In this respect bacterial or fungal enzymes are preferred, such as bacterial amylases and proteases, and fungal cellulases.

Enzymes are normally incorporated at levels sufficient to provide up to about 5 mg by weight, more typically about 0.01 mg to about 3 mg, of active enzyme per gram of the composition. Stated otherwise, the compositions herein will typically comprise from about 0.001% to about 5%, preferably 0.01%–1% by weight of a commercial enzyme preparation. Protease enzymes are usually present in such commercial preparations at levels sufficient to provide from 0.005 to 0.1 Anson units (AU) of activity per gram of composition.

Suitable examples of proteases are the subtilisins which are obtained from particular strains of *B. subtilis* and *B. licheniforms*. Another suitable protease is obtained from a strain of Bacillus, having maximum activity throughout the pH range of 8–12, developed and sold by Novo Industries A/S under the registered trade name ESPERASE. The preparation of this enzyme and analogous enzymes is described in British Patent Specification No. 1,243,784 of Novo. Proteolytic enzymes suitable for removing protein-based stains that are commercially available include those sold under the tradenames ALCALASE and SAVINASE by Novo Industries A/S (Denmark) and MAXATASE by International Bio-Synthetics, Inc. (The Netherlands). Other proteases include Protease A (see European Patent Application 130,756, published Jan. 9, 1985) and Protease B (see European Patent Application Serial No. 87303761.8, filed Apr. 28, 1987, and European Patent Application 130,756, Bott et al, published Jan. 9, 1985).

Amylases include, for example, α-amylases described in British Patent Specification No. 1,296,839 (Novo), RAPIDASE, International Bio-Synthetics, Inc. and TERMAMYL, Novo Industries.

The cellulase usable in the present invention include both bacterial or fungal cellulase. Preferably, they will have a pH optimum of between 5 and 9.5. Suitable cellulases are disclosed in U.S. Pat. No. 4,435,307, Barbesgoard et al, issued Mar. 6, 1984, which discloses fungal cellulase produced from Humicola insolens and Humicola strain DSM1800 or a cellulase 212-producing fungus belonging to the genus Aeromonas, and cellulase extracted from the hepatopancreas of a marine mollusk (Dolabella Auricula Solander). suitable cellulases are also disclosed in GB-A-2.075.028; GB-A-2.095.275 and DE-OS-2.247.832. CAREZYME (Novo) is especially useful.

Suitable lipase enzymes for detergent usage include those produced by microorganisms of the Pseudomonas group, such as *Pseudomonas stutzeri* ATCC 19.154, as disclosed in British Patent 1,372,034. See also lipases in Japanese Patent Application 53,20487, laid open to public inspection on Feb. 24, 1978. This lipase is available from Amano Pharmaceutical Co. Ltd., Nagoya, Japan, under the trade name Lipase P "Amano," hereinafter referred to as "Amano-P." Other commercial lipases include Amano-CES, lipases ex Chromobacter viscosum, e.g. Chromobacter viscosum var. lipolyticum NRRLB 3673, commercially available from Toyo Jozo Co., Tagata, Japan; and further Chromobacter viscosum lipases from U.S. Biochemical Corp., U.S.A. and Disoynth Co., The Netherlands, and lipases ex *Pseudomonas gladioli*. The LIPOLASE enzyme derived from *Humicola lanuginosa* and commercially available from Novo (see also EPO 341,947) is a preferred lipase for use herein.

Peroxidase enzymes are used in combination with oxygen sources, e.g., percarbonate, perborate, persulfate, hydrogen peroxide, etc. They are used for "solution bleaching," i.e. to prevent transfer of dyes or pigments removed from substrates during wash operations to other substrates in the wash solution. Peroxidase enzymes are known in the art, and include, for example, horseradish peroxidase, ligninase, and haloperoxidase such as chloro- and bromo-peroxidase. Peroxidase-containing detergent compositions are disclosed, for example, in PCT International Application WO 89/099813, published Oct. 19, 1989, by O. Kirk, assigned to Novo Industries A/S.

A wide range of enzyme materials and means for their incorporation into synthetic detergent compositions are also disclosed in U.S. Pat. No. 3,553,139, issued Jan. 5, 1971 to McCarty et al. Enzymes are further disclosed in U.S. Pat. No. 4,101,457, Place et al, issued Jul. 18, 1978, and in U.S. Pat. No. 4,507,219, Hughes, issued Mar. 26, 1985, both. Enzyme materials useful for liquid detergent formulations, and their incorporation into such formulations, are disclosed in U.S. Pat. No. 4,261,868, Hora et al, issued Apr. 14, 1981. Enzymes for use in detergents can be stabilized by various techniques. Enzyme stabilization techniques are disclosed and exemplified in U.S. Pat. No. 3,600,319, issued Aug. 17, 1971 to Gedge, et al, and European Patent Application Publication No. 0 199 405, Application No. 86200586.5, published Oct. 29, 1986, Venegas. Enzyme stabilization systems are also described, for example, in U.S. Pat. No. 3,519,570.

Enzyme Stabilizers—The enzymes employed herein are stabilized by the presence of water-soluble sources of calcium and/or magnesium ions in the finished compositions which provide such ions to the enzymes. (Calcium ions are generally somewhat more effective than magnesium ions and are preferred herein if only one type of cation is being used.) Additional stability can be provided by the presence of various other art-disclosed stabilizers, especially borate species: see Severson, U.S. Pat. No. 4,537,706. Typical detergents, especially liquids, will comprise from about 1 to about 30, preferably from about 2 to about 20, more preferably from about 5 to about 15, and most preferably from about 8 to about 12, millimoles of calcium ion per liter of finished composition. This can vary somewhat, depending on the amount of enzyme present and its response to the calcium or magnesium ions. The level of calcium or magnesium ions should be selected so that there is always some minimum level available for the enzyme, after allowing for complexation with builders, fatty acids, etc., in the composition. Any water-soluble calcium or magnesium salt can be used as the source of calcium or magnesium ions, including, but not limited to, calcium chloride, calcium sulfate, calcium malate, calcium maleate, calcium hydroxide, calcium formate, and calcium acetate, and the corresponding magnesium salts. A small amount of calcium ion, generally from about 0.05 to about 0.4 millimoles per liter, is often also present in the composition due to calcium in the enzyme slurry and formula water. In solid detergent compositions the formulation may include a sufficient quantity of a water-soluble calcium ion source to provide such amounts in the laundry liquor. In the alternative, natural water hardness may suffice.

It is to be understood that the foregoing levels of calcium and/or magnesium ions are sufficient to provide enzyme stability. More calcium and/or magnesium ions can be added to the compositions to provide an additional measure of grease removal performance. Accordingly, as a general proposition the compositions herein will typically comprise from about 0.05% to about 2% by weight of a water-soluble source of calcium or magnesium ions, or both. The amount can vary, of course, with the amount and type of enzyme employed in the composition.

The compositions herein may also optionally, but preferably, contain various additional stabilizers, especially borate-type stabilizers. Typically, such stabilizers will be used at levels in the compositions from about 0.25% to about 10%, preferably from about 0.5% to about 5%, more preferably from about 0.75% to about 3%, by weight of boric acid or other borate compound capable of forming boric acid in the composition (calculated on the basis of boric acid). Boric acid is preferred, although other compounds such as boric oxide, borax and other alkali metal borates (e.g., sodium ortho-, meta- and pyroborate, and sodium pentaborate) are suitable. Substituted boric acids (e.g., phenylboronic acid, butane boronic acid, and p-bromo phenylboronic acid) can also be used in place of boric acid.

Polymeric Soil Release Agent—Known polymeric soil release agents, hereinafter "SRA", can optionally be employed in the present detergent compositions. If utilized, SRA's will generally comprise from 0.01% to 10.0%, typically from 0.1% to 5%, preferably from 0.2% to 3.0% by weight, of the compositions.

Preferred SRA's typically have hydrophilic segments to hydrophilize the surface of hydrophobic fibers such as polyester and nylon, and hydrophobic segments to deposit upon hydrophobic fibers and remain adhered thereto through completion of washing and rinsing cycles, thereby serving as an anchor for the hydrophilic segments. This can enable stains occurring subsequent to treatment with the SRA to be more easily cleaned in later washing procedures.

SRA's can include a variety of charged, e.g., anionic or even cationic species, see U.S. Pat. No. 4,956,447, issued Sep. 11, 1990 to Gosselink, et al., as well as noncharged monomer units, and their structures may be linear, branched or even star-shaped. They may include capping moieties which are especially effective in controlling molecular weight or altering the physical or surface-active properties. Structures and charge distributions may be tailored for application to different fiber or textile types and for varied detergent or detergent additive products.

Preferred SRA's include oligomeric terephthalate esters, typically prepared by processes involving at least one transesterification/oligomerization, often with a metal catalyst such as a titanium(IV) alkoxide. Such esters may be made using additional monomers capable of being incorporated into the ester structure through one, two, three, four or more positions, without, of course, forming a densely crosslinked overall structure.

Suitable SRA's include a sulfonated product of a substantially linear ester oligomer comprised of an oligomeric ester backbone of terephthaloyl and oxyalkyleneoxy repeat units and allyl-derived sulfonated terminal moieties covalently attached to the backbone, for example as described in U.S. Pat. No. 4,968,451, Nov. 6, 1990 to J. J. Scheibel and E. P. Gosselink. Such ester oligomers can be prepared by: (a) ethoxylating allyl alcohol; (b) reacting the product of (a) with dimethyl terephthalate ("DMT") and 1,2-propylene glycol ("PG") in a two-stage transesterification/oligomerization procedure; and (c) reacting the product of (b) with sodium metabisulfite in water. Other SRA's include the nonionic end-capped 1,2-propylene/polyoxyethylene terephthalate polyesters of U.S. Pat. No. 4,711,730, Dec. 8, 1987 to Gosselink et al., for example those produced by transesterification/oligomerization of poly(ethyleneglycol) methyl ether, DMT, PG and poly(ethyleneglycol) ("PEG"). Other examples of SRA's include: the partly- and fully- anionic-end-capped oligomeric esters of U.S. Pat. No. 4,721,580, Jan. 26, 1988 to Gosselink, such as oligomers from ethylene glycol ("EG"), PG, DMT and Na-3,6-dioxa-8-hydroxyoctanesulfonate; the nonionic-capped block polyester oligomeric compounds of U.S. Pat. No. 4,702,857, Oct. 27, 1987 to Gosselink, for example produced from DMT, methyl (Me)-capped PEG and EG and/or PG, or a combination of DMT, EG and/or PG, Me-capped PEG and Na-dimethyl-5-sulfoisophthalate; and the anionic, especially sulfoaroyl, end-capped terephthalate esters of U.S. Pat. No. 4,877,896, Oct. 31, 1989 to Maldonado, Gosselink et al., the latter being typical of SRA's useful in both laundry and fabric conditioning products, an example being an ester composition made from m-sulfobenzoic acid monosodium salt, PG and DMT, optionally but preferably further comprising added PEG, e.g., PEG 3400.

SRA's also include: simple copolymeric blocks of ethylene terephthalate or propylene terephthalate with polyethylene oxide or polypropylene oxide terephthalate, see U.S. Pat. No. 3,959,230 to Hays, May 25, 1976 and U.S. Pat. No. 3,893,929 to Basadur, Jul. 8, 1975; cellulosic derivatives such as the hydroxyether cellulosic polymers available as METHOCEL from Dow; the $C_1$–$C_4$ alkyl celluloses and $C_4$ hydroxyalkyl celluloses, see U.S. Pat. No. 4,000,093, Dec. 28, 1976 to Nicol, et al.; and the methyl cellulose ethers having an average degree of substitution (methyl) per anhydroglucose unit from about 1.6 to about 2.3 and a solution viscosity of from about 80 to about 120 centipoise measured at 20° C. as a 2% aqueous solution. Such materials are available as METOLOSE SM100 and METOLOSE SM200, which are the trade names of methyl cellulose ethers manufactured by Shin-etsu Kagaku Kogyo KK.

Suitable SRA's characterised by poly(vinyl ester) hydrophobe segments include graft copolymers of poly(vinyl ester), e.g., $C_1$–$C_6$ vinyl esters, preferably poly(vinyl acetate), grafted onto polyalkylene oxide backbones. See European Patent Application 0 219 048, published Apr. 22, 1987 by Kud, et al. Commercially available examples include SOKALAN SRA's such as SOKALAN HP-22, available from BASF, Germany. Other SRA's are polyesters with repeat units containing 10-15% by weight of ethylene terephthalate together with 80–90% by weight of polyoxyethylene terephthalate derived from a polyoxyethylene glycol of average molecular weight 300–5,000. Commercial examples include ZELCON 5126 from Dupont and MILEASE T from ICI.

Another preferred SRA is an oligomer having empirical formula $(CAP)_2(EG/PG)_5(T)_5(SIP)_1$ which comprises terephthaloyl (T), sulfoisophthaloyl (SIP), oxyethyleneoxy and oxy-1,2-propylene (EG/PG) units and which is preferably terminated with end-caps (CAP), preferably modified isethionates, as in an oligomer comprising one sulfoisophthaloyl unit, 5 terephthaloyl units, oxyethyleneoxy and oxy-1,2-propyleneoxy units in a defined ratio, preferably about 0.5:1 to about 10:1, and two end-cap units derived from sodium 2-(2-hydroxyethoxy)-ethanesulfonate. Said SRA preferably further comprises from 0.5% to 20%, by weight of the oligomer, of a crystallinity-reducing stabiliser, for example an anionic surfactant such as linear sodium dodecylbenzenesulfonate or a member selected from xylene-, cumene-, and toluene- sulfonates or mixtures thereof, these stabilizers or modifiers being introduced into the synthesis vessel, all as taught in U.S. Pat. No. 5,415,807, Gosselink, Pan, Kellett and Hall, issued May 16, 1995. Suitable monomers for the above SRA include Na-2-(2-hydroxyethoxy)-ethanesulfonate, DMT, Na-dimethyl-5-sulfo-isophthalate, EG and PG.

Yet another group of preferred SRA's are oligomeric esters comprising: (1) a backbone comprising (a) at least one unit selected from the group consisting of dihydroxysulfonates, polyhydroxy sulfonates, a unit which is at least trifunctional whereby ester linkages are formed resulting in a branched oligomer backbone, and combinations thereof, (b) at least one unit which is a terephthaloyl moiety; and (c) at least one unsulfonated unit which is a 1,2-oxyalkyleneoxy moiety; and (2) one or more capping units selected from nonionic capping units, anionic capping units such as alkoxylated, preferably ethoxylated, isethionates, alkoxylated propanesulfonates, alkoxylated propanedisulfonates, alkoxylated phenolsulfonates, sulfoaroyl derivatives and mixtures thereof. Preferred are esters of the empirical formula:

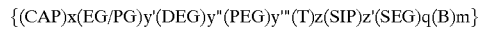

{(CAP)x(EG/PG)y'(DEG)y"(PEG)y'"(T)z(SIP)z'(SEG)q(B)m} wherein CAP, EG/PG, PEG, T and SIP are as defined hereinabove, (DEG) represents di(oxyethylene)oxy units, (SEG) represents units derived from the sulfoethyl ether of glycerin and related moiety units, (B) represents branching units which are at least trifunctional whereby ester linkages are formed resulting in a branched oligomer backbone, x is from about 1 to about 12, y' is from about 0.5 to about 25, y" is from 0 to about 12, y'" is from 0 to about 10, y'+y"+y'" totals from about 0.5 to about 25, z is from about 1.5 to about 25, z' is from 0 to about 12; z+z' totals from about 1.5 to about 25, q is from about 0.05 to about 12; m is from about 0.01 to about 10, and x, y', y", y'", z, z', q and m represent the average number of moles of the corresponding units per mole of said ester and said ester has a molecular weight ranging from about 500 to about 5,000.

Preferred SEG and CAP monomers for the above esters include Na-2-(2-,3-dihydroxypropoxy)ethanesulfonate ("SEG"), Na-2-{2-(2-hydroxyethoxy) ethoxy } ethanesulfonate ("SE3") and its homologs and mixtures thereof and the products of ethoxylating and sulfonating allyl alcohol. Preferred SRA esters in this class include the product of transesterifying and oligomerizing sodium 2-{2-(2-hydroxyethoxy)ethoxy }ethanesulfonate and/or sodium 2-[2-{2-(2-hydroxyethoxy)ethoxy}-ethoxy]ethanesulfonate, DMT, sodium 2-(2,3-dihydroxypropoxy) ethane sulfonate, EG, and PG using an appropriate Ti(IV) catalyst and can be designated as $(CAP)2(T)5(EG/PG)1.4(SEG)2.5(B)0.13$ wherein CAP is $(Na+—_3S[CH_2\text{-}CH_2O]3.5)$- and B is a unit from glycerin and the mole ratio EG/PG is about 1.7:1 as measured by conventional gas chromatography after complete hydrolysis.

Additional classes of SRA's include: (I) nonionic terephthalates using diisocyanate coupling agents to link polymeric ester structures, see U.S. Pat. No. 4,201,824, Violland et al. and U.S. Pat. No. 4,240,918 Lagasse et al.; and (II) SRA's with carboxylate terminal groups made by adding trimellitic anhydride to known SRA's to convert terminal hydroxyl groups to trimellitate esters. With the proper selection of catalyst, the trimellitic anhydride forms linkages to the terminals of the polymer through an ester of the isolated carboxylic acid of trimellitic anhydride rather than by opening of the anhydride linkage. Either nonionic or anionic SRA's may be used as starting materials as long as they have hydroxyl terminal groups which may be esterified. See U.S. Pat. No. 4,525,524 Tung et al. Other classes include: (III) anionic terephthalate-based SRA's of the urethane-linked variety, see U.S. Pat. No. 4,201,824, Violland et al.; (IV) poly(vinyl caprolactam) and related co-polymers with monomers such as vinyl pyrrolidone and/or dimethylaminoethyl methacrylate, including both nonionic and cationic polymers, see U.S. Pat. No. 4,579,681, Ruppert et al.; (V) graft copolymers, in addition to the SOKALAN types from BASF, made by grafting acrylic monomers onto sulfonated polyesters. These SRA's assertedly have soil release and anti-redeposition activity similar to known cellulose ethers: see EP 279,134 A, 1988, to Rhone-Poulenc Chemie. Still other classes include: (VI) grafts of vinyl monomers such as acrylic acid and vinyl acetate onto proteins such as caseins, see EP 457,205 A to BASF (1991); and (VII) polyester-polyamide SRA's prepared by condensing adipic acid, caprolactam, and polyethylene glycol, especially for treating polyamide fabrics, see Bevan et al., DE 2,335,044 to Unilever N. V., 1974. Other useful SRA's are described in U.S. Pat. Nos. 4,240,918, 4,787,989 and 4,525,524.

Chelating Agents—The compositions herein may also optionally contain one or more iron and/or manganese chelating agents. Such chelating agents can be selected from the group consisting of amino carboxylates, amino phosphonates, polyfunctionally-substituted aromatic chelating agents and mixtures therein, all as hereinafter defined. Without intending to be bound by theory, it is believed that the benefit of these materials is due in part to their exceptional ability to remove iron and manganese ions from washing solutions by formation of soluble chelates.

Amino carboxylates useful as optional chelating agents include ethylenediaminetetracetates, N-hydroxyethylethylenediaminetriacetates, nitrilotriacetates, ethylenediamine tetraproprionates, triethylenetetraaminehexacetates, diethylenetriaminepentaacetates, and ethanoldiglycines, alkali metal, ammonium, and substituted ammonium salts therein and mixtures therein.

Amino phosphonates are also suitable for use as chelating agents in the compositions of the invention when at lease low levels of total phosphorus are permitted in detergent compositions, and include ethylenediaminetetrakis (methylenephosphonates) as DEQUEST. Preferred, these amino phosphonates to not contain alkyl or alkenyl groups with more than about 6 carbon atoms.

Polyfunctionally-substituted aromatic chelating agents are also useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A preferred biodegradable chelator for use herein is ethylenediarine disuccinate ("EDDS"), especially the [S,S] isomer as described in U.S. Pat. No. 4,704,233, Nov. 3, 1987, to Hartman and Perkins.

If utilized, these chelating agents will generally comprise from about 0.1% to about 10% by weight of the detergent compositions herein. More preferably, if utilized, the chelating agents will comprise from about 0.1% to about 3.0% by weight of such compositions.

Clay Soil Removal/Anti-redeposition Agents—The compositions of the present invention can also optionally contain water-soluble ethoxylated amines having clay soil removal and antiredeposition properties. Granular detergent compositions which contain these compounds typically contain from about 0.01% to about 10.0% by weight of the water-soluble ethoxylates amines; liquid detergent compositions typically contain about 0.01% to about 5%.

The most preferred soil release and anti-redeposition agent is ethoxylated tetraethylenepentamine. Exemplary ethoxylated amines are further described in U.S. Pat. No. 4,597,898, VanderMeer, issued Jul. 1, 1986. Another group of preferred clay soil removal-antiredeposition agents are the cationic compounds disclosed in European Patent Application 111,965, Oh and Gosselink, published June 27, 1984. Other clay soil removal/antiredeposition agents which can be used include the ethoxylated amine polymers disclosed in European Patent Application 111,984, Gosselink, published Jun. 27, 1984; the zwitterionic polymers disclosed in European Patent Application 112,592, Gosselink, published Jul. 4, 1984; and the amine oxides disclosed in U.S. Pat. No. 4,548,744, Connor, issued Oct. 22, 1985. Other clay soil removal and/or anti redeposition agents known in the art can also be utilized in the compositions herein. Another type of preferred antiredeposition agent includes the carboxy methyl cellulose (CMC) materials. These materials are well known in the art.

Polymeric Dispersing Agents—Polymeric dispersing agents can advantageously be utilized at levels from about 0.1% to about 7%, by weight, in the compositions herein, especially in the presence of zeolite and/or layered silicate builders. Suitable polymeric dispersing agents include polymeric polycarboxylates and polyethylene glycols, although others known in the art can also be used. It is believed, though it is not intended to be limited by theory, that polymeric dispersing agents enhance overall detergent builder performance, when used in combination with other builders (including lower molecular weight polycarboxylates) by crystal growth inhibition, particulate soil release peptization, and anti-redeposition.

Polymeric polycarboxylate materials can be prepared by polymerizing or copolymerizing suitable unsaturated monomers, preferably in their acid form. Unsaturated monomeric acids that can be polymerized to form suitable polymeric polycarboxylates include acrylic acid, maleic acid (or maleic anhydride), fumaric acid, itaconic acid, aconitic acid, mesaconic acid, citraconic acid and methylenemalonic acid. The presence in the polymeric polycarboxylates herein or monomeric segments, containing no carboxylate radicals such as vinylmethyl ether, styrene, ethylene, etc. is suitable provided that such segments do not constitute more than about 40% by weight.

Particularly suitable polymeric polycarboxylates can be derived from acrylic acid. Such acrylic acid-based polymers which are useful herein are the water-soluble salts of polymerized acrylic acid. The average molecular weight of such polymers in the acid form preferably ranges from about 2,000 to 10,000, more preferably from about 4,000 to 7,000 and most preferably from about 4,000 to 5,000. Water-soluble salts of such acrylic acid polymers can include, for example, the alkali metal, ammonium and substituted ammonium salts. Soluble polymers of this type are known materials. Use of polyacrylates of this type in detergent compositions has been disclosed, for example, in Diehl, U.S. Pat. No. 3,308,067, issued Mar. 7, 1967.

Acrylic/maleic-based copolymers may also be used as a preferred component of the dispersing/anti-redeposition agent. Such materials include the water-soluble salts of copolymers of acrylic acid and maleic acid. The average molecular weight of such copolymers in the acid form preferably ranges from about 2,000 to 100,000, more preferably from about 5,000 to 75,000, most preferably from about 7,000 to 65,000. The ratio of acrylate to maleate segments in such copolymers will generally range from about 30:1 to about 1:1, more preferably from about 10:1 to 2:1. Water-soluble salts of such acrylic acid/maleic acid copolymers can include, for example, the alkali metal, ammonium and substituted ammonium salts. Soluble acrylate/maleate copolymers of this type are known materials which are described in European Patent Application No. 66915, published Dec. 15, 1982, as well as in EP 193,360, published Sep. 3, 1986, which also describes such polymers comprising hydroxypropylacrylate. Still other useful dispersing agents include the maleic/acrylic/vinyl alcohol terpolymers. Such materials are also disclosed in EP 193,360, including, for example, the 45/45/10 terpolymer of acrylic/maleic/vinyl alcohol.

Another polymeric material which can be included is polyethylene glycol (PEG). PEG can exhibit dispersing agent performance as well as act as a clay soil removal-antiredeposition agent. Typical molecular weight ranges for these purposes range from about 500 to about 100,000, preferably from about 1,000 to about 50,000, more preferably from about 1,500 to about 10,000.

Polyaspartate and polyglutamate dispersing agents may also be used, especially in conjunction with zeolite builders. Dispersing agents such as polyaspartate preferably have a molecular weight (avg.) of about 10,000.

Brightener—Any optical brighteners or other brightening or whitening agents known in the art can be incorporated at levels typically from about 0.01% to about 1.2%, by weight, into the detergent compositions herein. Commercial optical brighteners which may be useful in the present invention can be classified into subgroups, which include, but are not necessarily limited to, derivatives of stilbene, pyrazoline, coumarin, carboxylic acid, methinecyanines, dibenzothiophene-5,5-dioxide, azoles, 5- and 6-membered-ring heterocycles, and other miscellaneous agents. Examples of such brighteners are disclosed in "The Production and Application of Fluorescent Brightening Agents", M. Zahradnik, Published by John Wiley & Sons, New York (1982).

Specific examples of optical brighteners which are useful in the present compositions are those identified in U.S. Pat. No. 4,790,856, issued to Wixon on Dec. 13, 1988. These brighteners include the PHORWHITE series of brighteners from Verona. Other brighteners disclosed in this reference include: Tinopal UNPA, Tinopal CBS and Tinopal 5BM; available from Ciba-Geigy; Artic White CC and Artic White CWD, the 2-(4-styryl-phenyl)-2H-naptho[1,2-d]triazoles; 4,4'-bis-(1,2,3-triazol-2-yl)-stilbenes; 4,4'-bis(styryl) bisphenyls; and the amino-coumarins. Specific examples of these brighteners include 4-methyl-7-diethyl- amino coumarin; 1,2-bis(benzimidazol-2-yl)ethylene; 1,3-diphenyl-pyrazolines; 2,5-bis(benzoxazol-2-yl)thiophene; 2-styryl-naptho[1,2-d]oxazole; and 2-(stilben-4-yl)-2H-naphtho[1,2-d]triazole. See also U.S. Pat. No. 3,646,015, issued Feb. 29, 1972 to Hamilton.

Suds Suppressors—Compounds for reducing or suppressing the formation of suds can be incorporated into the compositions of the present invention. Suds suppression can be of particular importance in the so-called "high concentration cleaning process" as described in U.S. Pat. Nos. 4,489,455 and 4,489,574 and in front-loading European-style washing machines.

A wide variety of materials may be used as suds suppressors, and suds suppressors are well known to those skilled in the art. See, for example, Kirk Othmer Encyclopedia of Chemical Technology, Third Edition, Volume 7, pages 430–447 (John Wiley & Sons, Inc., 1979). One category of suds suppressor of particular interest encompasses monocarboxylic fatty acid and soluble salts therein. See U.S. Pat. No. 2,954,347, issued Sep. 27, 1960 to Wayne St. John. The monocarboxylic fatty acids and salts thereof used as suds suppressor typically have hydrocarbyl chains of 10 to about 24 carbon atoms, preferably 12 to 18 carbon atoms. Suitable salts include the alkali metal salts such as sodium, potassium, and lithium salts, and ammonium and alkanolammonium salts.

The detergent compositions herein may also contain non-surfactant suds suppressors. These include, for example: high molecular weight hydrocarbons such as paraffin, fatty acid esters (e.g., fatty acid triglycerides), fatty acid esters of monovalent alcohols, aliphatic $C_{18}$–$C_{40}$ ketones (e.g., stearone), etc. Other suds inhibitors include N-alkylated amino triazines such as tri- to hexa-alkylmelamines or di- to tetra-alkyldiamine chlortriazines formed as products of cyanuric chloride with two or three moles of a primary or secondary amine containing 1 to 24 carbon atoms, propylene oxide, and monostearyl phosphates such as monostearyl alcohol phosphate ester and monostearyl di-alkali metal (e.g., K, Na, and Li) phosphates and phosphate esters. The hydrocarbons such as paraffin and haloparaffin can be utilized in liquid form. The liquid hydrocarbons will be liquid at room temperature and atmospheric pressure, and will have a pour point in the range of about −40° C. and about 50° C., and a minimum boiling point not less than about 110° C. (atmospheric pressure). It is also known to utilize waxy hydrocarbons, preferably having a melting point below about 100° C. The hydrocarbons constitute a preferred category of suds suppressor for detergent compositions. Hydrocarbon suds suppressors are described, for example, in U.S. Pat. No. 4,265,779, issued May 5, 1981 to Gandolfo et al. The hydrocarbons, thus, include aliphatic, alicyclic, aromatic, and heterocyclic saturated or unsaturated hydrocarbons having from about 12 to about 70 carbon atoms. The term "paraffin," as used in this suds suppressor discussion, is intended to include mixtures of true paraffins and cyclic hydrocarbons.

Another preferred category of non-surfactant suds suppressors comprises silicone suds suppressors. This category includes the use of polyorganosiloxane oils, such as polydimethylsiloxane, dispersions or emulsions of polyorganosiloxane oils or resins, and combinations of polyorganosiloxane with silica particles wherein the polyorganosiloxane is chemisorbed or fused onto the silica. Silicone suds suppressors are well known in the art and are, for example, disclosed in U.S. Pat. No. 4,265,779, issued May 5, 1981 to Gandolfo et al and European Patent Application No. 89307851.9, published Feb. 7, 1990, by Starch, M. S.

Other silicone suds suppressors are disclosed in U.S. Pat. No. 3,455,839 which relates to compositions and processes for defoaming aqueous solutions by incorporating therein small amounts of polydimethylsiloxane fluids.

Mixtures of silicone and silanated silica are described, for instance, in German Patent Application DOS 2,124,526. Silicone defoamers and suds controlling agents in granular detergent compositions are disclosed in U.S. Pat. No. 3,933,672, Bartolotta et al, and in U.S. Pat. No. 4,652,392, Baginski et al, issued Mar. 24, 1987.

An exemplary silicone based suds suppressor for use herein is a suds suppressing amount of a suds controlling agent consisting essentially of:

(i) polydimethylsiloxane fluid having a viscosity of from about 20 cs. to about 1,500 cs. at 25° C.;

(ii) from about 5 to about 50 parts per 100 parts by weight of (i) of siloxane resin composed of $(CH_3)_3SiO_{1/2}$ units of $SiO_2$ units in a ratio of from $(CH_3)_3 SiO_{1/2}$ units and to $SiO_2$ units of from about 0.6:1 to about 1.2:1; and (iii) from about 1 to about 20 parts per 100 parts by weight of (i) of a solid silica gel.

In the preferred silicone suds suppressor used herein, the solvent for a continuous phase is made up of certain polyethylene glycols or polyethylene-polypropylene glycol copolymers or mixtures thereof (preferred), or polypropylene glycol. The primary silicone suds suppressor is branched/crosslinked and preferably not linear.

To illustrate this point further, typical liquid laundry detergent compositions with controlled suds will optionally comprise from about 0.001 to about 1, preferably from about 0.01 to about 0.7, most preferably from about 0.05 to about 0.5, weight % of said silicone suds suppressor, which comprises (1) a nonaqueous emulsion of a primary antifoam agent which is a mixture of (a) a polyorganosiloxane, (b) a resinous siloxane or a silicone resin-producing silicone compound, (c) a finely divided filler material, and (d) a catalyst to promote the reaction of mixture components (a), (b) and (c), to form silanolates; (2) at least one nonionic silicone surfactant; and (3) polyethylene glycol or a copolymer of polyethylene-polypropylene glycol having a solubility in water at room temperature of more than about 2 weight %; and without polypropylene glycol. Similar amounts can be used in granular compositions, gels, etc. See also U.S. Pat. No. 4,978,471, Starch, issued Dec. 18, 1990, and U.S. Pat No. 4,983,316, Starch, issued Jan. 8, 1991, U.S. Pat. No. 5,288,431, Huber et al., issued Feb. 22, 1994, and U.S. Pat. Nos. 4,639,489 and 4,749,740, Aizawa et al at column 1, line 46 through column 4, line 35.

The silicone suds suppressor herein preferably comprises polyethylene glycol and a copolymer of polyethylene glycot/polypropylene glycol, all having an average molecular weight of less than about 1,000, preferably between about 100 and 800. The polyethylene glycol and polyethylene/polypropylene copolymers herein have a solubility in water at room temperature of more than about 2 weight %, preferably more than about 5 weight %.

The preferred solvent herein is polyethylene glycol having an average molecular weight of less than about 1,000, more preferably between about 100 and 800, most preferably between 200 and 400, and a copolymer of polyethylene glycol/polypropylene glycol, preferably PPG 200/PEG 300. Preferred is a weight ratio of between about 1:1 and 1:10, most preferably between 1:3 and 1:6, of polyethylene glycol:copolymer of polyethylene-polypropylene glycol.

The preferred silicone suds suppressors used herein do not contain polypropylene glycol, particularly of 4,000 molecular weight. They also preferably do not contain block copolymers of ethylene oxide and propylene oxide, like PLURONIC L101.

Other suds suppressors useful herein comprise the secondary alcohols (e.g., 2-alkyl alkanols) and mixtures of such alcohols with silicone oils, such as the silicones disclosed in U.S. Pat. Nos. 4,798,679, 4,075,118 and EP 150,872. The secondary alcohols include the $C_6$–$C_{16}$ alkyl alcohols having a $C_1$–$C_{16}$ chain. A preferred alcohol is 2-butyl octanol, which is available from Condea under the trademark ISOFOL 12. Mixtures of secondary alcohols are available under the trademark ISALCHEM 123 from Enichem. Mixed suds suppressors typically comprise mixtures of alcohol+silicone at a weight ratio of 1:5 to 5:1.

For any detergent containing compositions to be used in automatic laundry washing machines, suds should not form to the extent that they overflow the washing machine. Suds suppressors, when utilized, are preferably present in a "suds suppressing amount." By "suds suppressing amount" is meant that the formulator of the composition can select an amount of this suds controlling agent that will sufficiently control the suds to result in a low-sudsing laundry detergent for use in automatic laundry washing machines.

The compositions herein will generally comprise from 0% to about 5% of suds suppressor. When utilized as suds suppressors, monocarboxylic fatty acids, and salts therein, will be present typically in amounts up to about 5%, by weight, of the detergent composition. Preferably, from about 0.5% to about 3% of fatty monocarboxylate suds suppressor is utilized. Silicone suds suppressors are typically utilized in amounts up to about 2.0%, by weight, of the detergent composition, although higher amounts may be used. This upper limit is practical in nature, due primarily to concern with keeping costs minimized and effectiveness of lower amounts for effectively controlling sudsing. Preferably from about 0.01% to about 1% of silicone suds suppressor is used, more preferably from about 0.25% to about 0.5%. As used herein, these weight percentage values include any silica that may be utilized in combination with polyorganosiloxane, as well as any adjunct materials that may be utilized. Monostearyl phosphate suds suppressors are generally utilized in amounts ranging from about 0.1% to about 2%, by weight, of the composition. Hydrocarbon suds suppressors are typically utilized in amounts ranging from about 0.01% to about 5.0%, although higher levels can be used. The alcohol suds suppressors are typically used at 0.2%–3% by weight of the finished compositions.

Fabric Softeners—Various through-the-wash fabric softeners, especially the impalpable smectite clays of U.S. Pat. No. 4,062,647, Storm and Nirschl, issued Dec. 13, 1977, as well as other softener clays known in the art, can optionally be used typically at levels of from about 0.5% to about 10% by weight in the present compositions to provide fabric softener benefits concurrently with fabric cleaning. Clay softeners can be used in combination with amine and cationic softeners as disclosed, for example, in U.S. Pat. No. 4,375,416, Crisp et al, Mar. 1, 1983 and U.S. Pat. No. 4,291,071, Harris et al, issued Sep. 22, 1981.

Dye Transfer Inhibiting Agents—The compositions of the present invention may also include one or more materials effective for inhibiting the transfer of dyes from one fabric to another during the cleaning process. Generally, such dye transfer inhibiting agents include polyvinyl pyrrolidone polymers, polyamine N-oxide polymers, copolymers of N-vinylpyrrolidone and N-vinylimidazole, manganese phthalocyanine, peroxidases, and mixtures thereof. If used, these agents typically comprise from about 0.01% to about 10% by weight of the composition, preferably from about 0.01% to about 5%, and more preferably from about 0.05% to about 2%.

More specifically, the polyamine N-oxide polymers preferred for use herein contain units having the following structural formula: R—$A_x$—P; wherein P is a polymerizable unit to which an N—O group can be attached or the N—O group can form part of the polymerizable unit or the N—O group can be attached to both units; A is one of the following structures: —NC(O)—, —C(O)O—, —S—, —O—, —N=; x is 0 or 1; and R is aliphatic, ethoxylated aliphatics, aromatics, heterocyclic or alicyclic groups or any combination thereof to which the nitrogen of the N—O group can be attached or the N—O group is part of these groups. Preferred polyamine N-oxides are those wherein R is a heterocyclic group such as pyridine, pyrrole, imidazole, pyrrolidine, piperidine and derivatives thereof.

The N—O group can be represented by the following general structures:

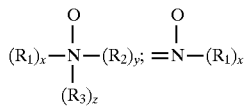

wherein $R_1$, $R_2$, $R_3$ are aliphatic, aromatic, heterocyclic or alicyclic groups or combinations thereof; x, y and z are 0 or 1; and the nitrogen of the N—O group can be attached or form part of any of the aforementioned groups. The amine oxide unit of the polyamine N-oxides has a pKa <10, preferably pKa <7, more preferred pKa <6.

Any polymer backbone can be used as long as the amine oxide polymer formed is water-soluble and has dye transfer inhibiting properties. Examples of suitable polymeric backbones are polyvinyls, polyalkylenes, polyesters, polyethers, polyamide, polyimides, polyacrylates and mixtures thereof. These polymers include random or block copolymers where one monomer type is an amine N-oxide and the other monomer type is an N-oxide. The amine N-oxide polymers typically have a ratio of amine to the amine N-oxide of 10:1 to 1:1,000,000. However, the number of amine oxide groups present in the polyamine oxide polymer can be varied by appropriate copolymerization or by an appropriate degree of N-oxidation. The polyamine oxides can be obtained in almost any degree of polymerization. Typically, the average molecular weight is within the range of 500 to 1,000,000; more preferred 1,000 to 500,000; most preferred 5,000 to 100,000. This preferred class of materials can be referred to as "PVNO".

The most preferred polyamine N-oxide useful in the detergent compositions herein is poly(4-vinylpyridine-N-oxide) which as an average molecular weight of about 50,000 and an amine to amine N-oxide ratio of about 1:4.

Copolymers of N-vinylpyrrolidone and N-vinylimidazole polymers (referred to as a class as "PVPVI") are also preferred for use herein. Preferably the PVPVI has an average molecular weight range from 5,000 to 1,000,000, more preferably from 5,000 to 200,000, and most preferably from 10,000 to 20,000. (The average molecular weight range is determined by light scattering as described in Barth, et al., *Chemical Analysis*, Vol 113. "Modern Methods of Polymer Characterization", the disclosures of which are incorporated herein by reference.) The PVPVI copolymers typically have a molar ratio of N-vinylimidazole to N-vinylpyrrolidone from 1:1 to 0.2:1, more preferably from 0.8:1 to 0.3:1, most preferably from 0.6:1 to 0.4:1. These copolymers can be either linear or branched.

The present invention compositions also may employ a polyvinylpyrrolidone ("PVP") having an average molecular weight of from about 5,000 to about 400,000, preferably from about 5,000 to about 200,000, and more preferably from about 5,000 to about 50,000. PVP's are known to persons skilled in the detergent field; see, for example, EP-A-262,897 and EP-A-256,696, incorporated herein by reference. Compositions containing PVP can also contain polyethylene glycol ("PEG") having an average molecular weight from about 500 to about 100,000, preferably from about 1,000 to about 10,000. Preferably, the ratio of PEG to PVP on a ppm basis delivered in wash solutions is from about 2:1 to about 50:1, and more preferably from about 3:1 to about 10:1.

The detergent compositions herein may also optionally contain from about 0.005% to 5% by weight of certain types of hydrophilic optical brighteners which also provide a dye transfer inhibition action. If used, the compositions herein will preferably comprise from about 0.01% to 1% by weight of such optical brighteners.

The hydrophilic optical brighteners useful in the present invention are those having the structural formula:

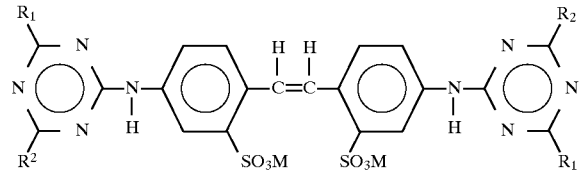

wherein $R_1$ is selected from anilino, N-2-bis-hydroxyethyl and NH-2-hydroxyethyl; $R_2$ is selected from N-2-bis-hydroxyethyl, N-2-hydroxyethyl-N-methylamino, morphilino, chloro and amino; and M is a salt-forming cation such as sodium or potassium.

When in the above formula, $R_1$ is anilino, $R_2$ is N-2-bis-hydroxyethyl and M is a cation such as sodium, the brightener is 4,4'-bis[(4-anilino-6-(N-2-bis-hydroxyethyl)-s-triazine-2-yl)amino]-2,2'-stilbenedisulfonic acid and disodium salt. This particular brightener species is commercially marketed under the tradename Tinopal-UNPA-GX by Ciba-Geigy Corporation. Tinopal-UNPA-GX is the preferred hydrophilic optical brightener useful in the detergent compositions herein.

When in the above formula, $R_1$ is anilino, $R_2$ is N-2-hydroxyethyl-N-2-methylamino and M is a cation such as sodium, the brightener is 4,4'-bis[(4-anilino-6-(N-2-hydroxyethyl-N-methylamino)-s-triazine-2-yl)amino]2,2'-stilbenedisulfonic acid disodium salt. This particular brightener species is commercially marketed under the tradename Tinopal 5BM-GX by Ciba-Geigy Corporation.

When in the above formula, $R_1$ is anilino, $R_2$ is morphilino and M is a cation such as sodium, the brightener is 4,4'-bis[(4-anilino-6-morphilino-s-triazine-2-yl)amino]2,2'-stilbenedisulfonic acid, sodium salt. This particular brightener species is commercially marketed under the tradename Tinopal AMS-GX by Ciba Geigy Corporation.

The specific optical brightener species selected for use in the present invention provide especially effective dye transfer inhibition performance benefits when used in combination with the selected polymeric dye transfer inhibiting agents hereinbefore described. The combination of such selected polymeric materials (e.g., PVNO and/or PVPVI) with such selected optical brighteners (e.g., Tinopal UNPA-GX, Tinopal 5BM-GX and/or Tinopal AMS-GX) provides significantly better dye transfer inhibition in aqueous wash solutions than does either of these two detergent composition components when used alone. Without being bound by theory, it is believed that such brighteners work this way because they have high affinity for fabrics in the wash solution and therefore deposit relatively quick on these fabrics. The extent to which brighteners deposit on fabrics in the wash solution can be defined by a parameter called the "exhaustion coefficient". The exhaustion coefficient is in general as the ratio of a) the brightener material deposited on fabric to b) the initial brightener concentration in the wash liquor. Brighteners with relatively high exhaustion coefficients are the most suitable for inhibiting dye transfer in the context of the present invention.

Of course, it will be appreciated that other, conventional optical brightener types of compounds can optionally be used in the present compositions to provide conventional fabric "brightness" benefits, rather than a true dye transfer inhibiting effect. Such usage is conventional and well-known to detergent formulations.

Other Ingredients—A wide variety of other ingredients useful in detergent containing compositions can be included in the compositions herein, including other active ingredients, carriers, hydrotropes, processing aids, dyes or pigments, solvents for liquid formulations, solid fillers for bar compositions, etc. If high sudsing is desired, suds boosters such as the $C_{10}$–$C_{16}$ alkanolamides can be incorporated into the compositions, typically at 1%–10% levels. The $C_{10}$–$C_{14}$ monoethanol and diethanol amides illustrate a typical class of such suds boosters. Use of such suds boosters with high sudsing adjunct surfactants such as the amine oxides, betaines and sultaines noted above is also advantageous. If desired, soluble magnesium salts such as $MgCl_2$, $MgSO_4$, and the like, can be added at levels of, typically, 0.1%–2%, to provide additional suds and to enhance grease removal performance.

Various detersive ingredients employed in the present compositions optionally can be further stabilized by absorbing said ingredients onto a porous hydrophobic substrate, then coating said substrate with a hydrophobic coating. Preferably, the detersive ingredient is admixed with a surfactant before being absorbed into the porous substrate. In use, the detersive ingredient is released from the substrate into the aqueous washing liquor, where it performs its intended detersive function.

To illustrate this technique in more detail, a porous hydrophobic silica (trademark SIPERNAT D10, DeGussa) is admixed with a proteolytic enzyme solution containing 3%–5% of $C_{13-15}$ ethoxylated alcohol (EO 7) nonionic surfactant. Typically, the enzyme/surfactant solution is 2.5 X the weight of silica. The resulting powder is dispersed with stirring in silicone oil (various silicone oil viscosities in the range of 500–12,500 can be used). The resulting silicone oil dispersion is emulsified or otherwise added to the final detergent matrix. By this means, ingredients such as the aforementioned enzymes, bleaches, bleach activators, bleach catalysts, photoactivators, dyes, fluorescers, fabric conditioners and hydrolyzable surfactants can be "protected" for use in detergents, including liquid laundry detergent compositions.

Liquid detergent compositions can contain water and other solvents as carriers. Low molecular weight primary or secondary alcohols exemplified by methanol, ethanol, propanol, and isopropanol are suitable. Monohydric alcohols are preferred for solubilizing surfactant, but polyols such as those containing from 2 to about 6 carbon atoms and from 2 to about 6 hydroxy groups (e.g., 1,3-propanediol, ethylene glycol, glycerine, and 1,2-propanediol) can also be used. The compositions may contain from 5% to 90%, typically 10% to 50% of such carriers.

The detergent compositions herein will preferably be formulated such that, during use in aqueous cleaning operations, the wash water will have a pH of between about 6.5 and about 11, preferably between about 7.5 and 10.5. Liquid dishwashing product formulations preferably have a pH between about 6.8 and about 9.0. Laundry products are typically at pH 9–11. Techniques for controlling pH at recommended usage levels include the use of buffers, alkalis, acids, etc., and are well known to those skilled in the art.

The bleaching compositions of the present invention are ideally suited for use in laundry applications. Accordingly, the present invention includes a method for laundering a fabric. The method includes contacting a fabric to be laundered with a laundry solution. The fabric may comprise most any fabric capable of being laundered in normal consumer use conditions. The laundry solution includes the bleach booster as fully described above and a peroxygen source also as fully described above. The laundry solution may also include any of the above described additives to the bleaching composition such as detersive surfactants, chelates, and detersive enzymes. The solution preferably has a pH of from about 8 to about 10.5. The compositions are preferably employed at concentrations of from about 500 to about 10,000 ppm in solution. The water temperatures preferably range from about 0° C. to about 50° C. The water to fabric ratio is preferably from about 1:1 to about 15:1

The bleach boosters of the present invention may also be employed in a laundry additive product. A laundry additive product including the bleach boosters of the present invention would be ideally suited for inclusion in a wash process when additional bleaching effectiveness is desired. Such instances may include, but are not limited to, low-temperature solution laundry application. The additive product may comprise in its simplest form a bleach booster as fully described above. Preferably, the additive could be packaged in dosage form for addition to a laundry process where a source of peroxygen is employed and increased bleaching effectiveness is desired. Such single dosage form may comprise a pill, tablet, gelcap or other single dosage unit such as pre-measured powders or liquids. A filler or carrier material may be included to increase the volume of composition if desired. Suitable filler or carrier materials may be selected from but not limited to various salts of sulfate, carbonate and silicate as well as talc, clay and the like. Filler or carrier materials for liquid compositions may be water or low molecular weight primary and secondary alcohols including polyols and diols. Examples include methanol, ethanol, propanol and isopropanol. Monohydric alcohols may also be employed. The compositions may contain from about 5% to about 90% of such materials. Acidic fillers can be used to reduce pH. Alternatively, the laundry additive may include a peroxygen source as defined above or various other additional ingredients as fully defined above. Laundry additives can also include powdered or liquid compositions containing a hydrogen peroxide source or a peroxygen source as defined above.

In an additional embodiment of the present invention, a bleaching solution comprising a solution of an oxaziridinium zwitterionic bleaching species is provided for. The oxaziridinium bleaching species is present in the solution in an amount which is sufficient to effect bleaching of a substrate placed in contact with the solution. The oxaziridinium compound is preferably derived from an aryliminium compound. The oxaziridinium bleaching species is the bleaching species formed from the reaction of the peroxygen source and the quaternary imine bleach booster as thoroughly described herein and is preferably represented by the formula:

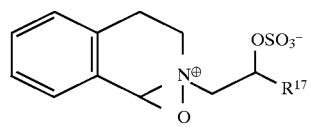

wherein $R^{17}$ is defined as above. The bleaching solution may further include any of the additional ingredients such as detersive surfactants, detersive enzymes and the like, as fully described herein.

The bleaching solution including the oxaziridinium bleaching species may, like the bleaching composition including the bleach booster, be employed in a number of different uses and environments. Preferably, the bleaching solution including the oxaziridinium compound is employed in a method for bleaching a fabric substrate. The method comprises contacting a fabric substrate to be bleached or laundered with a bleaching solution comprising the oxaziridinium compound. The contact takes place for a sufficient period of time under normal consumer use conditions to effect bleaching or laundering of the fabric substrate.

The bleaching composition of the present invention can be used in both low density (below 550 grams/liter) and high density granular compositions in which the density of the granule is at least 550 grams/liter. Low density compositions can be prepared by standard spray-drying processes. Various means and equipment are available to prepare high density compositions. Current commercial practice in the field employs spray-drying towers to manufacture compositions which have a density less than about 500 g/l. Accordingly, if spray-drying is used as part of the overall process, the resulting spray-dried particles must be further densified using the means and equipment described hereinafter. In the alternative, the formulator can eliminate spray-drying by using mixing, densifying and granulating equipment that is commercially available. The following is a nonlimiting description of such equipment suitable for use herein.

High speed mixer/densifiers can be used in the present process. For example, the device marketed under the trademark "Lodige CB30" Recycler comprises a static cylindrical mixing drum having a central rotating shaft with mixing/cutting blades mounted thereon. Other such apparatus includes the devices marketed under the trademark "Shugi Granulator" and under the trademark "Drais K_TTP 80." Equipment such as that marketed under the trademark "Lodige KM600 Mixer" can be used for further densification.

In one mode of operation, the compositions are prepared and densified by passage through two mixer and densifier machines operating in sequence. Thus, the desired compositional ingredients can be admixed and passed through a Lodige mixture using residence times of 0.1 to 1.0 minutes then passed through a second Lodige mixer using residence times of 1 minute to 5 minutes.

In another mode, the aqueous slurry comprising the desired formulation ingredients is sprayed into a fluidized bed of particulates. The resulting particles can be further densified by passage through a Lodige apparatus, as noted above. The delivery particles are mixed with the composition in the Lodige apparatus.

The final density of the particles herein can be measured by a variety of simple techniques, which typically involve dispensing a quantity of the granular composition into a container of known volume, measuring the weight of the composition and reporting the density in grams/liter. Once the low or high density "base" composition is prepared, the agglomerated delivery system is added thereto by any suitable dry-mixing operation.

The present invention will now be described by reference to the following examples. Of course, one of ordinary skill in the art will recognize that the present invention is not limited to the specific examples herein described or the ingredients and steps contained therein, but rather, may be practiced according to the broader aspects of the disclosure.

EXAMPLE I

Preparation of 1-(3,4-dihydroisoquinolinium)-decane-2-sulfate (5):

Step 1: Preparation of 3,4-dihydroisoquinoline (2):

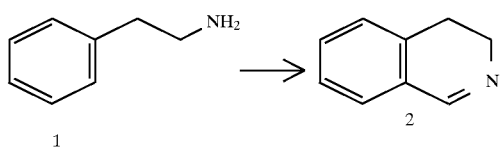

A 100 mL round bottom flask equipped with stir bar and distillation apparatus is charged with phenethylamine (1, 0.0413 mol) and 88% formic acid (7.6 g, 3.5 equiv.) and the reaction is distilled or refluxed at approximately 100° C. Beginning after one hour, additional 2 mL aliquots of 88% formic acid are added at approximately 30 minute intervals until the phenethylamine is consumed, as monitored by gas chromatography. The reaction mixture is distilled (using a Dean-Stark trap) at approximately 200° C. for approximately 45 minutes after which it is allowed to cool to room temperature.

A 250 mL round bottom flask equipped with stir bar, reflux condenser, and an addition funnel is charged with phosphorus pentoxide (7.07 g) and polyphosphoric acid in a 10.5:1 weight ratio. The mixture is stirred and heated at approximately 180° C. for about 1 hour, then cooled to approximately 150° C. The cooled, crude phenethylformamide prepared as described above is added dropwise to this mixture. On complete addition the reaction is heated and stirred at approximately 170° C. overnight. The mixture is cooled to room temperature and diluted with water (300 mL), washed with diethyl ether (150 mL) and cooled in an acetone/dry ice bath while the pH is adjusted to 9 with saturated potassium hydroxide. The aqueous solution is extracted with ether (3×150 mL) and the pooled organics are dried over magnesium sulfate, filtered, and concentrated under reduced pressure to yield an oil that is further purified via Kugelrohr distillation (70° C., 1 mm Hg) to give the compound of formula 2.

Step 2: Preparation of 1,2-decanediol cyclic sulfate (4):

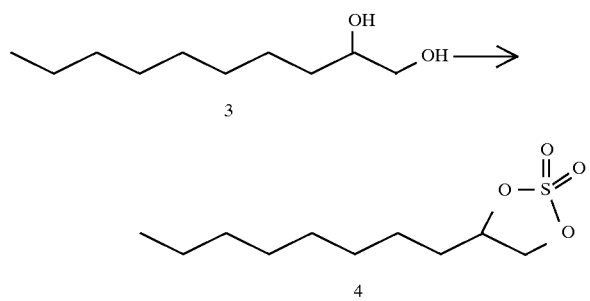

A three-neck, 500 mL round bottom flask equipped with mechanical stirrer, pressure equalizing addition funnel, and reflux condenser with Drierite® filled drying tube is charged with 1,2-decanediol (3, 8.72 g, 50.0 mmol) and 50 mL of carbon tetrachloride. When the 1,2-decanediol is dissolved, thionyl chloride (5.5 mL, 75 mmol) is added dropwise at room temperature and the reaction is heated to approximately 60° C. After two hours, the reaction is slowly cooled to about 0° C. Deionized water (50 mL) and acetonitrile (75 mL) are added. Ruthenium chloride hydrate (0.13 g, 0.50 mmol) and sodium periodate (21.4 g, 100 mmol) are added and the reaction mixture is stirred at room temperature for 1 h. The mixture is extracted with diethyl ether (4×175 mL), the organics are washed with deionized water (5×100 mL), saturated sodium bicarbonate solution (3×100 mL), and brine (2×100 mL), then filtered through celite/silica gel. The filtrate is dried over magnesium sulfate, filtered and concentrated via rotary evaporation to a clear oil.

Step 3: Preparation of 1-(3,4-dihydroisoquinolinium)-decane-2-sulfate (5)

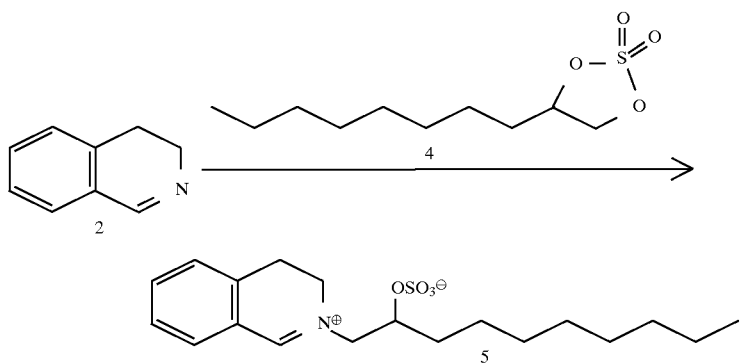

A 100 mL round bottom flask equipped with magnetic stir bar is charged with 3,4-dihydroisoquinoline (2.02 g, 15.4 mmol) and acetonitrile (15.2 mL). To this is added all at once 1,2-decanediol cyclic sulfate (3.78 g, 16.0 mmole). As the reaction mixture thickens, additional acetonitrile (60 mL) is added and the reaction is stirred overnight. The precipitate is collected, washed five times with acetone, and allowed to air dry.

EXAMPLE II

Preparation of 1-(3,4-dihydroisoquinolinium)-3,3-dimethylbutane-2-sulfate (6):

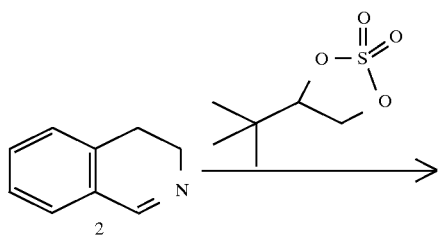

The procedure is the same as in EXAMPLE I except that 3,3-dimethyl-1,2-butanediol is substituted for 1,2-decanediol, giving 3,3-dimethyl-1,2-butanediol cyclic sulfate. This cyclic sulfate is substituted for 1,2-decanediol cyclic sulfate and reacted with 3,4-dihydroisoquinoline as in EXAMPLE I to give the desired product of formula 6.

EXAMPLE III

Preparation of 1-(3,4-dihydroisoquinolinium)-hexane-2-sulfate (7):

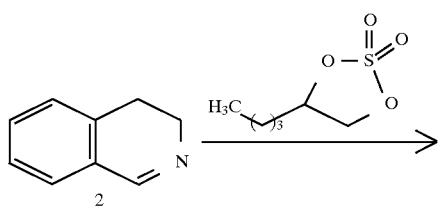

-continued

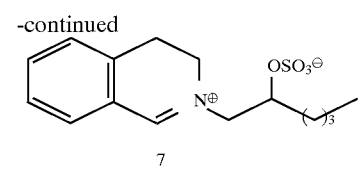

The procedure is the same as in EXAMPLE I except that 1,2-hexanediol is substituted for 1,2-decanediol, giving 1,2-hexanediol cyclic sulfate. This cyclic sulfate is substituted for 1,2-decanediol cyclic sulfate and reacted with 3,4-dihydroisoquinoline as in EXAMPLE I to give the desired product of formula 7.

EXAMPLE IV

Preparation of 1-(3,4-dihydroisoquinolinium)-octane-2-sulfate (8):

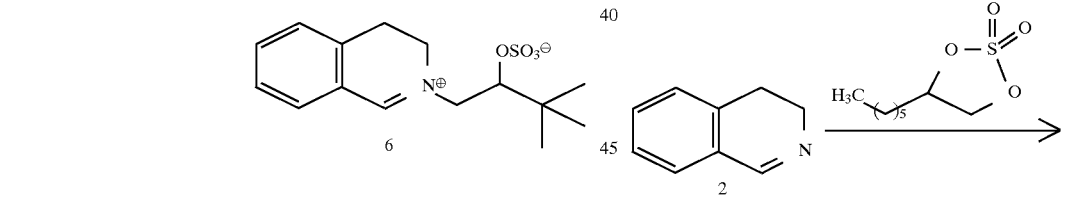

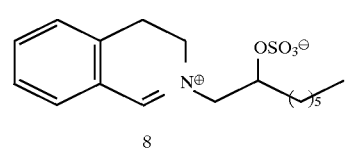

The procedure is the same as in EXAMPLE I except that 1,2-octanediol is substituted for 1,2-decanediol, giving 1,2-octanediol cyclic sulfate. This cyclic sulfate is substituted for 1,2-decanediol cyclic sulfate and reacted with 3,4-dihydroisoquinoline as in EXAMPLE I to give the desired product of formula 8.

EXAMPLE V

Preparation of 1-(3,4-dihydroisoquinolinium)-dodecane-2-sulfate (9):

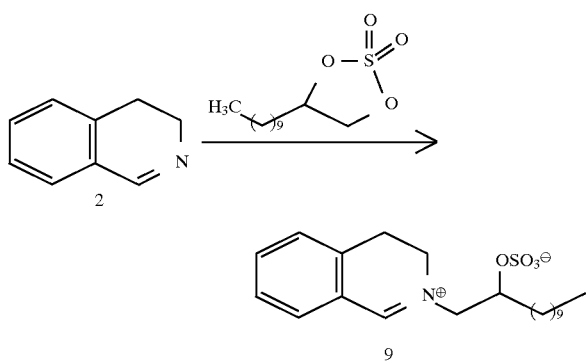

The procedure is the same as in EXAMPLE I except that 1,2-dodecanediol is substituted for 1,2-decanediol, giving 1,2-dodecanediol cyclic sulfate. This cyclic sulfate is substituted for 1,2-decanediol cyclic sulfate and reacted with 3,4-dihydroisoquinoline as in EXAMPLE I to give the desired product of formula 9.

EXAMPLE VI

Preparation of 1-(3,4-dihydroisoquinolinium)-tetradecane-2-sulfate (10):

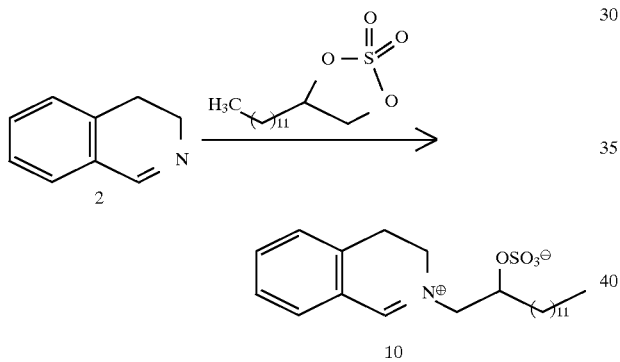

The procedure is the same as in EXAMPLE I except that 1,2-tetradecanediol is substituted for 1,2-decanediol, giving 1,2-tetradecanediol cyclic sulfate. This cyclic sulfate is substituted for 1,2-decanediol cyclic sulfate and reacted with 3,4-dihydroisoquinoline as in EXAMPLE I to give the desired product of formula 10.

EXAMPLE VII

Preparation of 1-(3,4-dihydroisoquinolinium)-hexadecane-2-sulfate (11):

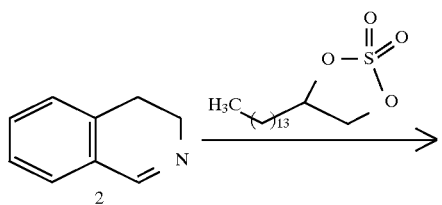

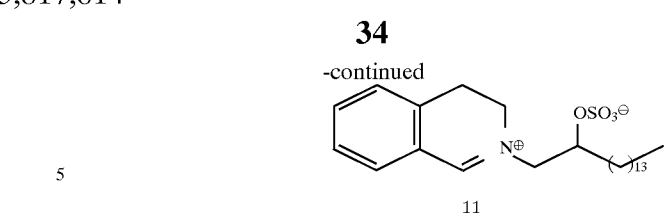

The procedure is the same as in EXAMPLE I except that 1,2-hexadecanediol is substituted for 1,2-decanediol, giving 1,2-hexadecanediol cyclic sulfate. This cyclic sulfate is substituted for 1,2-decanediol cyclic sulfate and reacted with 3,4-dihydroisoquinoline as in EXAMPLE I to give the desired product of formula 11.

EXAMPLE VIII

Preparation of 1-(3,4-dihydroisoquinolinium)-2-phenylethane-2-sulfate (12):

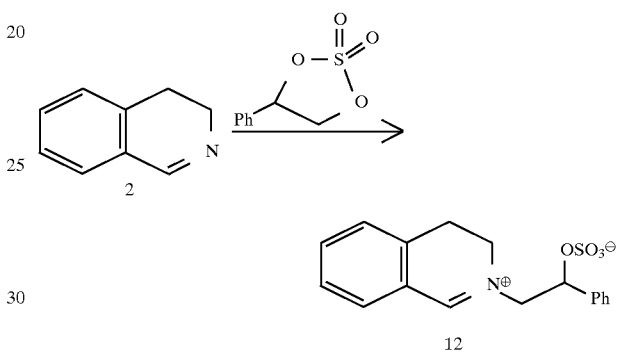

The procedure is the same as in EXAMPLE I except that 1-phenyl-1,2-ethanediol is substituted for 1,2-decanediol, giving 1-phenyl-1,2-ethanediol cyclic sulfate. This cyclic sulfate is substituted for 1,2-decanediol cyclic sulfate and reacted with 3,4-dihydroisoquinoline as in EXAMPLE I to give the desired product of formula 12.

EXAMPLE IX

Bleaching detergent compositions having the form of granular laundry detergents are exemplified by the following formulations.

|  | A | B | C | D | E |
|---|---|---|---|---|---|
| Bleach Booster* | 0.14 | 0.40 | 0.14 | 0.20 | 0.07 |
| Sodium Percarbonate | 5.30 | 0.00 | 0.00 | 4.00 | 0.00 |
| Sodium Perborate Monohydrate | 0.00 | 5.30 | 3.60 | 0.00 | 4.30 |
| Linear Alkylbenzenesulfonate | 12.00 | 0.00 | 12.00 | 0.00 | 21.00 |
| C45AE0.6S | 0.00 | 15.00 | 0.00 | 15.00 | 0.00 |
| C2 Dimethylamine N-Oxide | 0.00 | 2.00 | 0.00 | 2.00 | 0.00 |
| C12 Coco Amidopropyl Betaine | 1.50 | 0.00 | 1.50 | 0.00 | 0.00 |
| Palm N-Methyl Glucamide | 1.70 | 2.00 | 1.70 | 2.00 | 0.00 |
| C12 Dimethyl-hydroxyethylammonium Chloride | 1.50 | 0.00 | 1.50 | 0.00 | 0.00 |
| AE23-6.5T | 2.50 | 3.50 | 2.50 | 3.50 | 1.00 |
| C25E3S | 4.00 | 0.00 | 4.00 | 0.00 | 0.00 |
| Conventional Activator (NOBS) | 0.00 | 0.00 | 0.60 | 0.00 | 0.00 |
| Conventional Activator (TAED) | 2.00 | 2.80 | 2.00 | 1.80 | 2.30 |

-continued

|  | A | B | C | D | E |
|---|---|---|---|---|---|
| Sodium Tripolyphosphate | 25.00 | 25.00 | 15.00 | 15.00 | 25.00 |
| Zeolite A | 0.00 | 0.00 | 0.00 | 0.00 | 0.00 |
| Acrylic Acid/Maleic Acid Copolymer | 0.00 | 0.00 | 0.00 | 0.00 | 1.00 |
| Polyacrylic Acid, partially neutralized | 3.00 | 3.00 | 3.00 | 3.00 | 0.00 |
| Soil Release Agent | 0.00 | 0.00 | 0.50 | 0.40 | 0.00 |
| Carboxymethylcellulose | 0.40 | 0.40 | 0.40 | 0.40 | 0.40 |
| Sodium Carbonate | 2.00 | 2.00 | 2.00 | 0.00 | 8.00 |
| Sodium Silicate | 3.00 | 3.00 | 3.00 | 3.00 | 6.00 |
| Sodium Bicarbonate | 5.00 | 5.00 | 5.00 | 5.00 | 5.00 |
| Savinase (4T) | 1.00 | 1.00 | 1.00 | 1.00 | 0.60 |
| Termamyl (60T) | 0.40 | 0.40 | 0.40 | 0.40 | 0.40 |
| Lipolase (100T) | 0.12 | 0.12 | 0.12 | 0.12 | 0.12 |
| Carezyme (5T) | 0.15 | 0.15 | 0.15 | 0.15 | 0.15 |
| Diethylenetriaminepenta-(methylenephosphonic Acid) | 1.60 | 1.60 | 1.60 | 1.60 | 0.40 |
| Brightener | 0.20 | 0.20 | 0.20 | 0.05 | 0.20 |
| Sulfonated Zinc Phthalocyanine Photobleach | 0.50 | 0.00 | 0.25 | 0.00 | 0.00 |
| $MgSO_4$ | 2.20 | 2.20 | 2.20 | 2.20 | 0.64 |
| $Na_2SO_4$ | balance | balance | balance | balance | balance |

*A compound prepared according to any of EXAMPLES I–VIII.

Any of the above compositions is used to launder fabrics at a concentration of 3500 ppm in water, 25° C., and a 15:1 water:cloth ratio. The typical pH is about 9.5 but can be adjusted by altering the proportion of acid to Na— salt form of alkylbenzenesulfonate.

EXAMPLE X

Bleaching detergent compositions having the form of granular laundry detergents are exemplified by the following formulations.

|  | A | B | C | D | E |
|---|---|---|---|---|---|
| Bleach Booster* | 0.06 | 0.34 | 0.14 | 0.14 | 0.20 |
| Sodium Percarbonate | 5.30 | 0.00 | 0.00 | 0.00 | 0.00 |
| Sodium Perborate Monohydrate | 0.00 | 9.00 | 17.60 | 9.00 | 9.00 |
| Linear Alkylbenzenesulfonate | 21.00 | 12.00 | 0.00 | 12.00 | 12.00 |
| C45AE0.6S | 0.00 | 0.00 | 15.00 | 0.00 | 0.00 |
| C2 Dimethylamine N-Oxide | 0.00 | 0.00 | 2.00 | 0.00 | 0.00 |
| C12 Coco Amidopropyl Betaine | 0.00 | 1.50 | 0.00 | 1.50 | 1.50 |
| Palm N-Methyl Glucamide | 0.00 | 1.70 | 2.00 | 1.70 | 1.70 |
| C12 Dimethyl-hydroxyethylammonium Chloride | 1.00 | 1.50 | 0.00 | 1.50 | 1.50 |
| AE23-6.5T | 0.00 | 2.50 | 3.50 | 2.50 | 2.50 |
| C25E3S | 0.00 | 4.00 | 0.00 | 4.00 | 4.00 |
| Conventional Activator (NOBS) | 0.00 | 0.00 | 0.00 | 1.00 | 0.00 |
| Conventional Activator (TAED) | 1.80 | 1.00 | 2.50 | 3.00 | 1.00 |
| Sodium Tripolyphosphate | 25.00 | 15.00 | 25.00 | 15.00 | 15.00 |
| Zeolite A | 0.00 | 0.00 | 0.00 | 0.00 | 0.00 |
| Acrylic Acid/Maleic Acid Copolymer | 0.00 | 0.00 | 0.00 | 0.00 | 0.00 |
| Polyacrylic Acid, partially neutralized | 0.00 | 3.00 | 3.00 | 3.00 | 3.00 |
| Soil Release Agent | 0.30 | 0.50 | 0.00 | 0.50 | 0.50 |
| Carboxymethylcellulose | 0.00 | 0.40 | 0.40 | 0.40 | 0.40 |
| Sodium Carbonate | 0.00 | 2.00 | 2.00 | 2.00 | 2.00 |
| Sodium Silicate | 6.00 | 3.00 | 3.00 | 3.00 | 3.00 |
| Sodium Bicarbonate | 2.00 | 5.00 | 5.00 | 5.00 | 5.00 |
| Savinase (4T) | 0.60 | 1.00 | 1.00 | 1.00 | 1.00 |
| Termamyl (60T) | 0.40 | 0.40 | 0.40 | 0.40 | 0.40 |
| Lipolase (100T) | 0.12 | 0.12 | 0.12 | 0.12 | 0.12 |
| Carezyme (5T) | 0.15 | 0.15 | 0.15 | 0.15 | 0.15 |
| Diethylenetriaminepenta-(methylenephosphonic Acid) | 0.40 | 0.00 | 1.60 | 0.00 | 0.00 |
| Brightener | 0.20 | 0.30 | 0.20 | 0.30 | 0.30 |
| Sulfonated Zinc Phthalocyanine Photobleach | 0.25 | 0.00 | 0.00 | 0.00 | 0.00 |
| $MgSO_4$ | 0.64 | 0.00 | 2.20 | 0.00 | 0.00 |
| $Na_2SO_4$ | balance | balance | balance | balance | balance |

*A compound prepared according to any of EXAMPLES I–VIII.

Any of the above compositions is used to launder fabrics at a concentration of 3500 ppm in water, 25° C., and a 15:1 water-cloth ratio. The typical pH is about 9.5 but can be adjusted by altering the proportion of acid to Na— salt form of alkylbenzenesulfonate.

EXAMPLE XI

A bleaching detergent powder comprises the following ingredients:

| Component | Weight % |
|---|---|
| Bleach Booster* | 0.07 |
| TAED | 2.0 |
| Sodium Perborate Tetrahydrate | 10 |
| $C_{12}$ linear alkyl benzene sulfonate | 8 |
| Phosphate (as sodium tripolyphosphate) | 9 |
| Sodium carbonate | 20 |
| Talc | 15 |
| Brightener, perfume | 0.3 |
| Sodium Chloride | 25 |
| Water and Minors* | Balance to 100% |

*A compound prepared according to EXAMPLES I–VIII.

EXAMPLE XII

A laundry bar suitable for hand-washing soiled fabrics is prepared by standard extrusion processes and comprises the following:

| Component | Weight % |
|---|---|
| Bleach Booster* | 0.2 |
| TAED | 1.7 |
| NOBS | 0.2 |
| Sodium Perborate Tetrahydrate | 12 |
| $C_{12}$ linear alkyl benzene sulfonate | 30 |
| Phosphate (as sodium tripolyphosphate) | 10 |
| Sodium carbonate | 5 |
| Sodium pyrophosphate | 7 |
| Coconut monoethanolamide | 2 |
| Zeolite A (0.1–10 micron) | 5 |
| Carboxymethylcellulose | 0.2 |
| Polyacrylate (m.w. 1400) | 0.2 |
| Brightener, perfume | 0.2 |
| Protease | 0.3 |
| $CaSO_4$ | 1 |
| $MgSO_4$ | 1 |
| Water | 4 |
| Filler** | Balance to 100% |

| Component | Weight % |
|---|---|
| *A compound prepared according to any of EXAMPLES I–VIII. | |
| **Can be selected from convenient materials such as CaCO₃, talc, clay, silicates, and the like. Acidic fillers can be used to reduce pH. | |

EXAMPLE XIII

A laundry detergent composition suitable for machine use is prepared by standard methods and comprises the following composition:

| Component | Weight % |
|---|---|
| Bleach Booster* | 0.82 |
| TAED | 7.20 |
| Sodium Perborate Tetrahydrate | 9.2 |
| Sodium Carbonate | 23.74 |
| Anionic surfactant | 14.80 |
| Alumino Silicate | 21.30 |
| Silicate | 1.85 |
| Diethylenetriaminepentaacetic acid | 0.43 |
| Polyacrylic acid | 2.72 |
| Brightener | 0.23 |
| Polyethylene glycol solids | 1.05 |
| Sulfate | 8.21 |
| Perfume | 0.25 |
| Water | 7.72 |
| Processing aid | 0.10 |
| Miscellaneous | 0.43 |

*A compound prepared according to any of EXAMPLES I–VIII.

The composition is used to launder fabrics at a concentration in solution of about 1000 ppm at a temperature of 20°–40° C. and a water to fabric ratio of about 20:1.

EXAMPLE XIV

| Component | Weight % |
|---|---|
| Bleach Booster* | 1.0 |
| TAED | 10.0 |
| Sodium Perborate Tetrahydrate | 8.0 |
| Sodium Carbonate | 21.0 |
| Anionic surfactant | 12.0 |
| Alumino Silicate | 18.0 |
| Diethylenetriaminepentaacetic acid | 0.3 |
| Nonionic surfactant | 0.5 |
| Polyacrylic acid | 2.0 |
| Brightener | 0.3 |
| Sulfate | 17.0 |
| Perfume | 0.25 |
| Water | 6.7 |
| Miscellaneous | 2.95 |

*A compound prepared according to any of EXAMPLES I–VIII.

The composition is used to launder fabrics at a concentration in solution of about 1000 ppm at a temperature of 20°–40° C. and a water to fabric ratio of about 20:1.

What is claimed is:

1. A bleaching composition comprising:

a peroxygen source and a bleach booster having the formula:

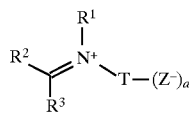

wherein $R^1$–$R^3$ is hydrogen or an unsubstituted or substituted radical selected from the group consisting of phenyl, aryl, heterocyclic ring, alkyl and cycloalkyl radicals; $R^1$ and $R^2$ form part of a common ring; T has the formula:

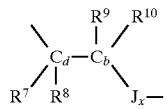

wherein x is equal to 0 or 1; J, when present, is selected from the group consisting of $-CR^{11}R^{12}-$, $-CR^{11}R^{12}CR^{13}R^{14}-$, and $-CR^{11}R^{12}CR^{13}R^{14}CR^{15}R^{16}-$; $R^7$–$R^{16}$ are selected from the group consisting of H, linear or branched $C_1$–$C_{18}$ substituted or unsubstituted alkyl, alkylene, oxyalkylene, aryl, substituted aryl, substituted arylcarbonyl groups, and amide groups; provided that at least one of $R^7$–$R^8$ must be H or methyl, and that when neither $R^9$ nor $R^{10}$ is H, one of $R^7$–$R^8$ must be H; Z is covalently bonded to $J_x$ when x is 1 and to $C_b$ when x is 0; and Z is selected from the group consisting of $-CO_2^-$, $-SO_3^-$ and $-OSO_3^-$, and a is 1; provided that when x is equal to 0, then at least one of $R^7$–$R^{10}$ is not H; and provided that when x is equal to 1, then at least one of $R^7$–$R^{16}$, when present, is not H.

2. The bleaching composition as claimed in claim 1 wherein said peroxygen source comprises a preformed peracid compound selected from the group consisting of percarboxylic acids and salts, percarbonic acids and salts, perimidic acids and salts, peroxymonosulfuric acids and salts, and mixtures thereof.

3. The bleaching composition as claimed in claim 1 wherein said peroxygen source comprises a hydrogen peroxide source and a bleach activator.

4. The bleaching composition as claimed in claim 3 wherein said hydrogen peroxide source is selected from the group consisting of perborate compounds, percarbonate compounds, perphosphate compounds and mixtures thereof.

5. The bleaching composition as claimed in claim 3 wherein said bleach activator is selected from the group consisting of tetraacetylethylenediamine, sodium decanoyloxybenzene sulfonate, sodium nonanoyloxybenzene sulfonate, sodium lauroyloxybenzene sulfonate, sodium octanoyloxybenzene sulfonate, (6-octanamido-caproyl) oxybenzenesulfonate, (6-nonanamido-caproyl) oxybenzenesulfonate, (6-decanamido-caproyl) oxybenzenesulfonate, and mixtures thereof.

6. The bleaching composition as claimed in claim 1 wherein $R_1$ and $R_2$ together form the non-charged moiety:

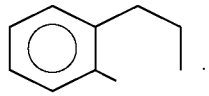

7. The bleaching composition as claimed in claim 6 wherein said bleach booster is an aryliminium zwitterion and $R^3$ is H, Z is $-OSO_3^-$, a is 1.

8. The bleaching composition as claimed in claim 7 wherein said bleach booster is an aryliminium zwitterion having the formula:

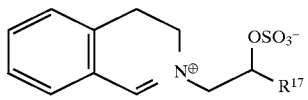

where $R^{17}$ is selected from the group consisting of H and linear or branched $C_1-C_{18}$ substituted or unsubstituted alkyl.

9. The bleaching composition as claimed in claim 1 further comprising at least one detersive surfactant.

10. The bleaching composition as claimed in claim 9 further comprising at least one chelating agent.

11. The bleaching composition as claimed in claim 1 further comprising at least one detersive enzyme.

12. The bleaching composition as claimed in claim 9 having an aqueous 1% solution pH of from about 8 to about 10.5.

13. A zwitterionic bleach booster compound selected from:

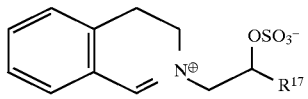

where $R^{17}$ is selected from the group consisting of linear or branched $C_1-C_{18}$ substituted or unsubstituted alkyl.

14. A laundry additive product comprising:

a laundry additive, said additive comprising a bleach booster having the formula:

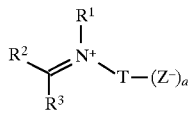

wherein $R^1-R^3$ is hydrogen or an unsubstituted or substituted radical selected from the group consisting of phenyl, aryl, heterocyclic ring, alkyl and cycloalkyl radicals; $R^1$ and R2 form part of a common ring; T has the formula:

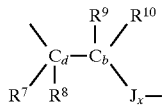

wherein x is equal to 0 or 1; J, when present, is selected from the group consisting of —$CR^{11}R^{12}$—, —$CR^{11}R^{12}CR^{13}R^{14}$—, and —$CR^{11}R^{12}CR^{13}R^{14}CR^{15}R^{16}$—; $R^7-R^{16}$ are selected from the group consisting of H, linear or branched $C_1-C_{18}$ substituted or unsubstituted alkyl, alkylene, oxyalkylene, aryl, substituted aryl, substituted arylcarbonyl groups, and amide groups; provided that at least one of $R^7-R^8$ must be H or methyl, and that when neither $R^9$ nor $R^{10}$ is H, one of $R^7-R^8$ must be H; Z is covalently bonded to $J_x$ when x is 1 and to $C_b$ when x is 0; and Z is selected from the group consisting of —$CO_2^-$, —$SO_3^-$ and —$OSO_3^-$, and a is 1; provided that when x is equal to 0, then at least one of $R^7-R^{10}$ is not H; and provided that when x is equal to 1, then at least one of $R^7-R^{16}$, when present, is not H; said additive being in dosage form for addition to a laundry solution.

15. The laundry product as claimed in claim 14 wherein said additive further comprises a hydrogen peroxide source selected from the group consisting of perborate compounds, percarbonate compounds, perphosphate compounds and mixtures thereof.

16. The laundry product as claimed in claim 15 wherein said additive further comprises a bleach activator selected from the group consisting of tetraacetylethylenediamine, sodium decanoyloxybenzene sulfonate, sodium nonanoyloxybenzene sulfonate, sodium lauroyloxybenzene sulfonate, sodium octanoyloxybenzene sulfonate, (6-octanamido-caproyl)oxybenzenesulfonate, (6-nonanamido-caproyl)oxybenzenesulfonate, (6-decanamido-caproyl)oxybenzenesulfonate, and mixtures thereof.

17. The laundry product as claimed in claim 14 wherein said bleach booster has the formula:

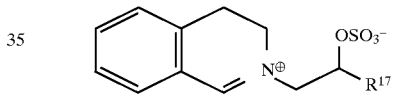

where $R^{17}$ is selected from the group consisting of H and linear or branched $C_1-C_{18}$ substituted or unsubstituted alkyl.

18. The laundry product as claimed in claim 14, wherein said dosage form comprises a pill, tablet, caplet, gelcap or other single dosage form.

19. The laundry product as claimed in claim 14 wherein said laundry additive further includes a suitable carrier.

* * * * *

UNITED STATES PATENT AND TRADEMARK OFFICE
CERTIFICATE OF CORRECTION

PATENT NO. : 5,817,614
DATED : October 6, 1998
INVENTOR(S) : Gregory Scot Miracle
　　　　　　　Robert Richard Dykstra It is certified that error appears in the above-identified patent and that said Letters Patent is hereby corrected as shown below:

Column 38, lines 64-67 of Claim #1 should read "1. A bleaching composition comprising: from about 0.01% to about 60% by weight of a peroxygen source and from about 0.01% to about 10% by weight of a bleach booster having the formula:"

Signed and Sealed this

Fourteenth Day of March, 2000

Attest:

Attesting Officer

Q. TODD DICKINSON

Commissioner of Patents and Trademarks